United States Patent
Jones et al.

(10) Patent No.: US 8,979,536 B2
(45) Date of Patent: Mar. 17, 2015

(54) PREFORMED MALLEABLE DENTAL ARTICLES AND METHODS

(75) Inventors: Todd D. Jones, St. Paul, MN (US); Sumita B. Mitra, West St. Paul, MN (US); Gerald S. Deeb, Mendota Heights, MN (US); Yufeng Liu, Woodbury, MN (US); Jie Yang, Woodbury, MN (US); Naimul Karim, Maplewood, MN (US); Dwight W. Jacobs, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 34 days.

(21) Appl. No.: 13/121,956

(22) PCT Filed: Nov. 17, 2009

(86) PCT No.: PCT/US2009/064685
§ 371 (c)(1),
(2), (4) Date: Mar. 31, 2011

(87) PCT Pub. No.: WO2010/057144
PCT Pub. Date: May 20, 2010

(65) Prior Publication Data
US 2011/0207087 A1    Aug. 25, 2011

Related U.S. Application Data

(60) Provisional application No. 61/115,276, filed on Nov. 17, 2008.

(51) Int. Cl.
| | |
|---|---|
| *A61C 5/08* | (2006.01) |
| *A61C 13/087* | (2006.01) |
| *A61C 5/00* | (2006.01) |
| *A61C 5/10* | (2006.01) |
| *A61C 13/08* | (2006.01) |

(Continued)

(52) U.S. Cl.
CPC .............. *A61C 13/087* (2013.01); *A61C 5/00* (2013.01); *A61C 5/10* (2013.01); *A61C 13/081* (2013.01); *A61C 13/20* (2013.01); *A61C 13/0001* (2013.01); *A61C 2201/00* (2013.01); *A61C 2202/00* (2013.01)
USPC ...................................... 433/222.1

(58) Field of Classification Search
USPC ........... 433/202.1–205, 209–213, 215–228.1; 264/16–19; 428/57, 98, 411.1
See application file for complete search history.

(56) References Cited

U.S. PATENT DOCUMENTS

| | | |
|---|---|---|
| 2,474,676 A | 6/1949 | Kelly |
| 5,403,188 A | 4/1995 | Oxman |

(Continued)

OTHER PUBLICATIONS

Kraton.com. KRATON Polymers Fact Sheet [retrieved on Nov. 1, 2013]. Retrieved from the Internet: http://docs.kraton.com/kraton/attachments/down loads/82021AM.pdf.*

(Continued)

*Primary Examiner* — Cris L Rodriguez
*Assistant Examiner* — Justin O'Donnell
(74) *Attorney, Agent, or Firm* — Carolyn A. Fischer

(57) ABSTRACT

A hardenable dental article including a base and at least one outer surface extending from the base, wherein at least the base and the at least one outer surface of the hardenable dental article includes a hardenable dental material; and a multi-layer polymeric film conformable release liner in contact with at least a portion of the at least one outer surface.

19 Claims, 2 Drawing Sheets

(51) Int. Cl.
*A61C 13/20* (2006.01)
*A61C 13/107* (2006.01)

(56) References Cited

U.S. PATENT DOCUMENTS

| | | | |
|---|---|---|---|
| 6,030,606 | A | 2/2000 | Holmes |
| 6,057,383 | A | 5/2000 | Völkel |
| 6,106,295 | A * | 8/2000 | Wilson .................. 433/222.1 |
| 6,436,529 | B1 | 8/2002 | Deeb |
| 6,799,969 | B2 | 10/2004 | Sun |
| 6,869,666 | B2 | 3/2005 | Deeb |
| 7,674,850 | B2 | 3/2010 | Karim |
| 7,811,486 | B2 | 10/2010 | Karim |
| 2003/0022010 | A1 | 1/2003 | Deeb |
| 2003/0114553 | A1* | 6/2003 | Karim et al. .................. 523/115 |
| 2003/0118804 | A1 | 6/2003 | Bedingham |
| 2003/0203339 | A1 | 10/2003 | Chilibeck |
| 2005/0100868 | A1 | 5/2005 | Karim |
| 2007/0196792 | A1* | 8/2007 | Johnson et al. ................ 433/218 |
| 2007/0264615 | A1 | 11/2007 | Ruppert |
| 2008/0293018 | A1 | 11/2008 | Karim |
| 2009/0305195 | A1 | 12/2009 | Jones |
| 2009/0305196 | A1 | 12/2009 | Karim |
| 2010/0062394 | A1 | 3/2010 | Jones |

OTHER PUBLICATIONS

International Search Report PCT/US2009/064685; Mar. 11, 2010, 3 pgs.

* cited by examiner

PREFORMED MALLEABLE DENTAL ARTICLES AND METHODS

CROSS REFERENCE TO RELATED APPLICATIONS

This application is a national stage filing under 35 U.S.C. 371 of PCT/US2009/064685, filed Nov. 17, 2009, which claims the benefit of U.S. Provisional Application No. 61/115,276, filed Nov. 17, 2008, which is incorporated herein by reference in its entirety.

BACKGROUND

Preformed dental articles are used extensively in restorative dentistry, which is an important market in the dental industry. In one example, tooth repair with temporary and permanent dental articles such as preformed crowns or bridges, is a common procedure, where the restoration process is expedited by using a preformed dental article in the shape being restored. Conventional technologies use liners, adhesives, pastes, two-part powder/liquid systems, preformed metal or polymer temporary crowns, and preformed ceramic or porcelain/metal permanent crowns. When a customized dental article is desired, multiple visits to a dentist are often required with such conventional technologies.

Adjustments to the preformed metal and polymer crowns can be made by removing material at the crown margin to obtain a desired crown length. Metal crowns may also be crimped at the cervical region to obtain good marginal adaptation. Modification of other crown dimensions, however, such as interproximal distances, crown anatomy, etc. are not performed because the materials used in the preformed crowns are not amenable to shape adjustment by the practitioner. As a result, these crowns are offered in a very large number of sizes, typically 36 or more for either the posterior or anterior teeth, to sufficiently cover the range of conditions encountered in a dental practice.

Hardenable dental materials, which are malleable and, thereby, customizable, have been developed to address some of these issues. For example, PROTEMP crowns are available from 3M ESPE, St. Paul, Minn.

With these advances and a growing interest in customizable preformed dental articles, there is a continuing need for improved customizable preformed dental articles and for a broader range of such customizable preformed dental articles.

SUMMARY

Protected hardenable dental articles, such as preformed hardenable dental crowns, can now be provided with a multi-layer polymeric film covering the outer surface of the hardenable dental article. In certain embodiments, the protected hardenable dental article may have a very high aspect ratio, such as that of an anterior crown. The multi-layer polymeric film comprises at least two dissimilar polymers in separate layers.

Accordingly, in one embodiment, there is provided a protected hardenable dental article comprising:

a hardenable dental article comprising a base and at least one outer surface extending from the base, wherein at least the base and the at least one outer surface of the hardenable dental article comprise a hardenable dental material; and a multi-layer polymeric film in contact with at least a portion of the at least one outer surface; wherein the multi-layer polymeric film comprises at least two dissimilar polymers in separate layers.

In another embodiment, there is provided a kit comprising a plurality of protected hardenable dental articles described above or a plurality of any of the embodiments of the protected hardenable dental articles described below.

In another embodiment, there is provided a method of manufacturing a protected hardenable dental article, the method comprising:

providing a first mold cavity in a shape of a hardenable dental article, wherein the first mold cavity comprises an opening and surfaces defining the shape, the surfaces extending from the opening;

forcing a hardenable dental material and a multi-layer polymeric film into the first mold cavity, wherein the multi-layer polymeric film is between the hardenable dental material and the surfaces defining the shape, and wherein the hardenable dental material is formed into the hardenable dental article comprising a base and at least one outer surface extending from the base, the surface corresponding to the first mold cavity surfaces defining the shape; and removing the hardenable dental article from the first mold cavity;

wherein the multi-layer polymeric film is in contact with at least a portion of the at least one outer surface; and wherein the multi-layer polymeric film comprises at least two dissimilar polymers in separate layers.

DEFINITIONS

The term "dental article" includes, for example, temporary, intermediate, and permanent crowns, bridges, implants, dentures, artificial teeth, inlays, onlays, veneers, orthodontic appliances, maxillofacial prosthesis, and tooth splints.

The term "malleable" refers, for example, to an article, such as a hardenable dental article, which can be custom-shaped and fitted under a moderate manual force (i.e., a force that ranges from light finger pressure to that applied with manual operation of a small hand tool, such as a dental composite instrument). The shaping, fitting, forming, etc., can be performed by adjusting the external shape and internal cavity shape of the hardenable dental article without adding material or removing material other than at or adjacent to the margin. In one example, the article can be fitted onto a prepared tooth. For certain embodiments, a malleable article is also self-supporting.

The term "self-supporting" as used herein refers to an article, for example a hardenable dental article, which is dimensionally stable and will maintain its shape without significant deformation at room temperature (i.e., about 20° C. to about 25° C.) for at least about two weeks when free-standing (i.e., without the support of packaging or a container, other than the multi-layer polymeric film). For certain embodiments, the article is preformed, such as a preformed crown. For certain embodiments, hardenable dental articles described herein are dimensionally stable at room temperature for at least about one month, or for at least about six months. For certain embodiments, hardenable dental articles described herein are dimensionally stable at temperatures above room temperature, or up to about 40° C., or up to about 50° C., or up to about 60° C. This definition applies in the absence of conditions that activate any initiator system and in the absence of an external force other than gravity.

The term "preformed" refers to an article, for example a hardenable dental article, which is formed in a shape, for example, the shape of a dental article, suitable for use with no customizing or with customizing, as required for any one particular application.

The term "recovery load" as used herein refers to a force exerted by a film, such as the multi-layer polymeric film, or a layer of a film, such as a layer of the multi-layer polymeric film, when stretched, such that the force tends to partially return the film to its unstretched dimension in the direction opposite the stretch direction.

The term "substantially deforming" as used herein refers to a dimension of an article, for example, a hardenable dental article, being different, for example 10% or more different or 20% or more different, than the corresponding dimension of the mold in which the dental article is formed.

The term "radially stretched" as used herein refers to a film, for example, a multi-layer polymeric film, stretched in two or more directions or in all directions over a radius of 360 degrees. "Radially stretched" includes but is not limited to biaxially stretched. The amount of stretch in each direction may be the same or different. Because of the irregular shape of at least some hardenable dental articles, the degree of stretch of a film protecting such hardenable dental articles is different in one or more directions than in other directions.

The term "elastic recovery" refers to the percent reduction in the maximum amount a film is stretched (extended) when the load at maximum stretch (extension) is reduced or removed.

The terms "load" or "tensile load" are expressed herein in units of force, for example, newtons (N).

The term "substantially the same" refers in typical embodiments of the present disclosure to a difference of not more than 20 percent, preferably not more than 10 percent, more preferably not more than 5 percent.

The term "comprising" and variations thereof (e.g., comprises, includes, etc.) do not have a limiting meaning where these terms appear in the description and claims.

As used herein, "a," "an," "the," "at least one," and "one or more" are used interchangeably, unless the context clearly dictates otherwise. As used in this specification and the appended claims, the term "or" is generally employed in its sense including "and/or" unless the content clearly dictates otherwise.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the present specification and attached claims are approximations that can vary depending upon the desired properties sought to be obtained by those skilled in the art utilizing the teachings disclosed herein.

Also herein, the recitation of numerical ranges by endpoints includes all numbers subsumed within that range (e.g. 1 to 5 includes 1, 1.5, 2, 2.75, 3, 3.80, 4, and 5) and any range within that range.

The above summary of the present invention is not intended to describe each disclosed embodiment or every implementation of the present invention. The description that follows more particularly exemplifies illustrative embodiments.

BRIEF DESCRIPTIONS OF THE DRAWINGS

DETAILED DESCRIPTION OF ILLUSTRATIVE EMBODIMENTS OF THE INVENTION

Figure 1A:
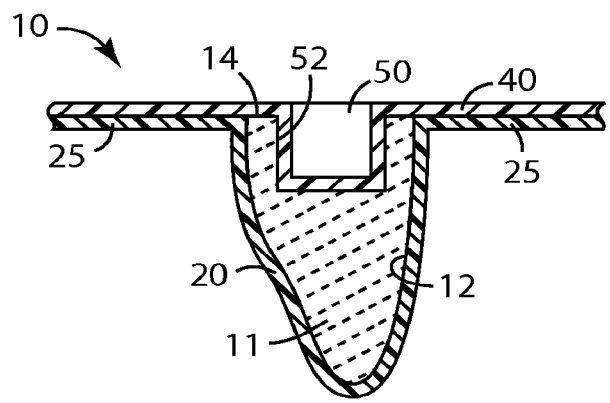
FIG. 1A is a cross-sectional view of an embodiment of a protected hardenable dental article of the present invention, preformed as an anterior crown, and including optional base liner.

It has now been found that, using certain multi-layer polymeric films as a conformable release liner, preformed, malleable, hardenable dental articles, such as preformed hardenable dental crowns, in certain embodiments including very high aspect ratio dental articles, for example, anterior crowns, can be manufactured. The multi-layer polymeric film comprises at least two dissimilar polymers in separate layers. The multi-layer polymeric films can provide a high radial stretch to accommodate a wide range of sizes of the hardenable dental articles. For certain embodiments, the multi-layer polymeric films provide a high radial stretch with a relatively low recovery load during elastic recovery. A low recovery load may prevent excessive deformation of the preformed hardenable dental article. For certain embodiments, preferably the multi-layer polymeric film prevents a hardenable dental material, typically a tacky composite, from being forced through the film and contacting a mold in which the preformed dental article is formed. Preventing appreciable amounts of tacky composite from contacting the mold can also prevent excessive deformation of the preformed hardenable dental article when removed from the mold. Moreover, the multi-layer polymeric film can protect the article during handling and shipping as well as during application by the practitioner.

The protected hardenable dental articles described herein comprise a hardenable dental material. For certain embodiments, including any one of the article, kit, or method embodiments herein, this material is malleable at temperatures of 40° C. to 15° C. For certain of these embodiments, the hardenable dental material is malleable in a temperature range of 38° C. to room temperature.

In many embodiments, the hardenable dental materials of the preformed dental articles described herein are irreversibly hardenable such that after hardening the material loses its malleability and cannot be converted back into a malleable form without destroying the external shape of the dental article.

Examples of some potentially suitable hardenable dental materials that may be used to construct the hardenable dental articles described herein with sufficient malleability may include, for example, hardenable organic compositions (filled or unfilled), polymerizable dental waxes, hardenable dental compositions having a wax-like or clay-like consistency in the unhardened state, and the like. In some embodiments, the hardenable dental articles are constructed of hardenable compositions that consist essentially of non-metallic materials.

Suitable hardenable dental materials that may be used to manufacture the hardenable dental articles described herein include, for example, compositions described in U.S. Patent Application Publication No. US 2003/0114553, titled HARDENABLE SELF-SUPPORTING STRUCTURES AND METHODS (Karim et al.). Other suitable hardenable compositions may include those described in U.S. Pat. No. 5,403,188 (Oxman et al.); U.S. Pat. No. 6,057,383 (Volkel et al.); and U.S. Pat. No. 6,799,969 (Sun et al.).

Organogelators described in International Publication No. WO 2008/033911 titled DENTAL COMPOSITIONS INCLUDING ORGANOGELATORS, PRODUCTS, AND METHODS can be included with the hardenable dental materials in the dental articles described herein. These organogelator compositions can be flowable, packable, or self-supporting. The term "organogelator" refers to a low molecular weight compound (generally no greater than 3000 grams per mole) that forms a three-dimensional network structure when dissolved in an organic fluid, thereby immobilizing the organic fluid and forming a non-flowable thermally-reversible gel.

With respect to the hardenable compositions described in US 2003/0114553, the unique combination of highly malleable properties (preferably without heating above room temperature or body temperature) before hardening (e.g., curing) and high strength (preferably, e.g., a flexural strength of at least about 25 MPa) after hardening may provide hardenable dental articles with numerous potential advantages.

As discussed herein, the hardenable dental article, which is typically preformed, and the hardenable dental materials are sufficiently malleable to facilitate forming of the hardenable dental article onto, for example, a prepared tooth during the fitting process. Because the materials are hardenable, the adjusted shape can be retained.

For certain embodiments, the hardenable dental material of any one of the embodiments described herein is a photopolymerizable composite comprising a resin system, a filler system, and an initiator system, and wherein the photopolymerizable composite is self-supporting and malleable. For certain embodiments, the hardenable dental material of any one of the embodiments described herein is a hardenable composition of US 2003/0114553. For certain of these embodiments, the hardenable composition includes a resin system that includes a crystalline component, greater than 60 percent by weight (wt-%) of a filler system (preferably, greater than 70 wt-% of a filler system), and an initiator system, wherein the hardenable composition exhibits sufficient malleability to be formed onto a prepared tooth, preferably at a temperature of about 15° C. to 38° C. (more preferably, about 20° C. to 38° C., which encompasses typical room temperatures and body temperatures). In some embodiments, the hardenable compositions do not need to be heated above body temperature (or even about room temperature) to become malleable as discussed herein.

For certain embodiments, at least a portion of the filler system of the hardenable compositions of US 2003/0114553 includes particulate filler. For certain embodiments, including embodiments which include a particulate filler, the filler system further includes fibers. For certain of these embodiments, the fibers are present in an amount of less than 20 weight percent (wt-%), based on the total weight of the composition.

The crystalline component may provide a morphology that assists in maintaining a self-supporting first shape. This morphology includes a non-covalent structure, which may be a three-dimensional network (continuous or discontinuous) structure. If desired, the crystalline component can include one or more reactive groups to provide sites for polymerizing and/or crosslinking If such crystalline components are not present or do not include reactive groups, such reactive sites are provided by another resin component, such as an ethylenically unsaturated component.

Thus, for certain embodiments, the resin system includes at least one ethylenically unsaturated component. Ethylenically unsaturated components can be selected from the group consisting of mono-, di-, or poly-acrylates, mono-, di-, or poly-methacrylates, unsaturated amides, vinyl compounds (including vinyl oxy compounds), and combinations thereof. This ethylenically unsaturated component can be the crystalline component or non-crystalline.

The crystalline component can include polyesters, polyethers, polyolefins, polythioethers, polyarylalkylenes, polysilanes, polyamides, polyurethanes, or combinations thereof. The crystalline component can include saturated, linear, aliphatic polyester polyols containing primary hydroxyl end groups. The crystalline component can optionally have a dendritic, hyperbranched, or star-shaped structure, for example.

The crystalline component can optionally be a polymeric material (i.e., a material having two or more repeat units, including oligomeric materials) having crystallizable pendant moieties and the following general formula (I):

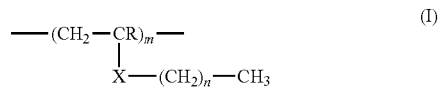

wherein R is hydrogen or a $C_{1-4}$ alkyl group, X is —$CH_2$—, —C(O)—O—, —O—C(O)—, —C(O)—NH—, —HN—C(O)—, —O—, —NH—, —O—C(O)—NH—, —HN—C(O)—O, —HN—C(O)—NH—, or —Si$(CH_3)_2$—, m is the number of repeating units in the polymer (preferably, 2 or more), and n is an integer great enough so that sufficient side chain length and conformation are provided to form polymers containing crystalline domains or regions.

As an alternative to, or in combination with, the crystalline component, the hardenable dental material can include a filler that is capable of providing a morphology to the composition that includes a non-covalent structure, which may be a three-dimensional network (continuous or discontinuous) structure, that assists in the maintenance of the first shape. For certain embodiments, such a filler comprises nanoparticles, or the filler is an inorganic material comprising nanoparticles. For certain embodiments, the nanoparticles have a mean or average diameter of less than 200 nm or less than 100 nm. To enhance the formation of the non-covalent structure, the inorganic material can include surface hydroxyl groups. For certain embodiments, the inorganic material includes fumed silica.

The use of one or more surfactants can also enhance the formation of such a non-covalent structure. For certain embodiments, the composition includes, in addition to a resin system and an initiator system, either a crystalline component, or a filler system that includes nanoparticles or both micron-size particles and nanoparticles and a surfactant system, or both a crystalline component and a filler system and a surfactant system. As used herein, a filler system includes one or more fillers and a surfactant system includes one or more surfactants.

For certain embodiments, the hardenable dental material that may be used in the preformed dental articles of the invention may include a hardenable composition of U.S.

Patent Application Publication No. 2003/0114553 that includes a resin system, a filler system, at least a portion of which is an inorganic material having nanoparticles with an average primary particle size of no greater than about 50 nanometers (nm), a surfactant system, and an initiator system. The hardenable composition can exhibit sufficient malleability to be formed onto a prepared tooth at a temperature of about 15° C. to 38° C. In embodiments with a surfactant system and nanoparticles, the resin system can include at least one ethylenically unsaturated component, and the filler system is present in an amount greater than 50 wt-%.

For certain embodiments, the hardenable dental material includes a resin system comprising a noncrystalline component selected from the group consisting of mono-, di-, or poly-acrylates, mono-, di-, or poly-methacrylates, unsaturated amides, vinyl compounds, and combinations thereof; and a crystalline component selected from the group consisting of polyesters, polyethers, polyolefins, polythioethers, polyarylalkylenes, polysilanes, polyamides, polyurethanes, polymeric materials (including oligomeric materials) having crystallizable pendant moieties with the above general formula I, and combinations thereof. For certain of these embodiments, the hardenable dental material further includes greater than about 60 wt-% of a filler system, and an initiator system. The hardenable composition can exhibit sufficient malleability to be formed onto a prepared tooth at a temperature of about 15° C. to 38° C. For certain embodiments, at least a portion of the filler system of the hardenable composition includes particulate filler. For certain embodiments, including embodiments which include a particulate filler, the filler system further includes fibers. For certain of these embodiments, the fibers are present in an amount of less than 20 weight percent (wt-%), based on the total weight of the composition.

For certain embodiments, the hardenable dental material includes a resin system with a crystalline compound of the following formula (II):

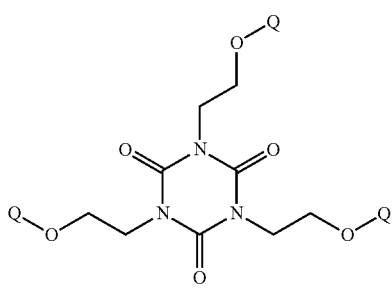

II wherein each Q independently comprises polyester segments, polyamide segments, polyurethane segments, polyether segments, or combinations thereof; a filler system; and an initiator system.

For certain embodiments, including any one of the article, kit, and method embodiments described herein, the hardenable dental material has a paste hardness of not less than 400 g, preferably not less than 500 g. For certain of these embodiments, the hardenable dental material has a paste hardness of not more than 4000 grams, preferably not more than 2500 g. For certain of these embodiments, the hardenable dental material has a paste hardness of 500 to 2500 g. For certain of these embodiments, the paste hardness is 500 to 1500 g. Alternatively, for certain of these embodiments, the hardenable dental material has a paste hardness of 1200 to 2500 g.

The protected hardenable dental articles described herein also comprise a multi-layer polymeric film in contact with at least a portion of the at least one outer surface of the hardenable dental article. For certain embodiments, the film is in intimate contact with substantially all of the outer surface(s) of the hardenable dental article.

Suitable multi-layer polymeric films comprise at least two dissimilar polymers in separate layers. For example, an outer layer may comprise at least one polymer, and an inner core layer may comprise at least one polymer that is different than at least one polymer comprising the outer layer. For certain embodiments, including any one of the article, kit, and method embodiments described herein, the dissimilar polymers differ from each other in a characteristic selected from the group consisting of composition, crystallinity, modulus, maximum elongation, recovery load, surface energy, an optical property, and a combination thereof. Examples of polymers dissimilar in composition may include elastic and plastic polymers, homopolymers and copolymers, polymers of different molecular weights, polymers of different densities, one type of polymer and another type of polymer, for example, polyethylene and sytrene-isoprene-styrene block copolymer, different molecular structure (e.g., linear vs. branched), different amounts of a polymer, different phase morphology, and the like. Crystallinity differences may arise due to differences in comonomer content, differences in branching, differences in molecular weight, and the like. Crystallinity differences may translate to different elongation, modulus, density, and/or recovery properties in the separate layers. Surface energy differences may provide good release from the hardenable dental article and/or from a mold while providing good adhesion between layers. Optical properties include, for example, transparency, opacity, percent haze, surface gloss, color, and the like.

For certain embodiments, including any one of the article, kit, and method embodiments described herein, the dissimilar polymers are dissimilar in composition. For certain of these embodiments, the dissimilar polymers are elastic and plastic polymers and/or different types of polymers.

For certain embodiments, including any one of the article, kit, and method embodiments described herein, the dissimilar polymers are dissimilar in modulus.

For certain embodiments, including any one of the article, kit, and method embodiments described herein, the dissimilar polymers are dissimilar in recovery load.

For certain embodiments, including any one of the article, kit, and method embodiments described herein, the multi-layer polymeric film has a relatively high visible light transmittance, for example, at least 90 percent transmittance and relatively low haze, for example, less than 10 percent haze.

For certain embodiments, including any one of the article, kit, and method embodiments described herein, the separate layers have different thicknesses. For certain of these embodiments, the separate layers have a thickness ratio of 1:2 to 1:100, preferably 1:3 to 1:50, more preferably 1:5 to 1:20. For certain of these embodiments, the separate layers are an outer layer and a core layer. For certain of these embodiments, these ratios refer to the ratio of an outer layer thickness to a core layer thickness.

For certain embodiments, including any one of the article, kit, and method embodiments described herein the separate layers have different surface energies. For certain of these embodiments, the separate layers are an outer layer and a core layer. For certain of these embodiments, the outer layer has a lower surface energy than the core layer.

The hardenable dental articles described herein encompass a variety of sizes and shapes and are further described herein below. In one example, the protected hardenable dental article is a preformed crown. Various crowns require various degrees of radial stretching. For example, a pediatric upper molar may require approximately 375 percent or more radial stretching. In another example, a pediatric lower molar may require more than 400 percent radial stretching. In other examples, a pediatric canine or an adult upper molar may require more than 550 percent radial stretching, an adult upper incisor or an adult lower molar may require more than 600 percent radial stretching, and an adult lower incisor may require more than 800 percent radial stretching.

For certain embodiments, including any one of the above article, kit, or method embodiments, the multi-layer polymeric film can be radially stretched by the hardenable dental article to an area which is at least 350 percent of the area of the multi-layer polymeric film prior to being radially stretched. For certain of these embodiments, the multi-layer polymeric film can be radially stretched by the hardenable dental article to an area which is at least 550 percent of the area of the multi-layer polymeric film prior to being radially stretched. For certain of these embodiments, the multi-layer polymeric film can be radially stretched by the hardenable dental article to an area which is at least 800 percent of the area of the multi-layer polymeric film prior to being radially stretched. In one alternative, for certain of these embodiments, the multi-layer polymeric film is radially stretched by the hardenable dental article to an area 550 to 850 percent of the area of the multi-layer polymeric film prior to being radially stretched. For certain of these embodiments, the multi-layer polymeric film is radially stretched by the hardenable dental article to an area 600 to 850 percent of the area of the multi-layer polymeric film prior to being radially stretched.

After being radially stretched, the film used in making the hardenable dental article tends to undergo an elastic recovery and exerts a recovery load on the hardenable dental article. When the recovery load is sufficiently low and/or the hardenable dental article can provide sufficient resistance to the recovery load, the elastic recovery is insufficient to cause excessive or significant deformation of the article. Parameters which predict sufficiently low elastic recovery and recovery load as well as sufficient radial stretch and sufficiently low load when stretched to the necessary extent have now been found and can be conveniently determined by measuring tensile properties of the film.

For certain embodiments, including any one of the above article, kit, or method embodiments, the multi-layer polymeric film has an elastic recovery of not more than 85 percent at a tensile load of less than 0.044 newtons after recovery from a maximum extension of at least 325 percent. For certain of these embodiments, the elastic recovery is after recovery from a maximum extension of at least 600 percent. For certain of these embodiments, where the maximum extension is at least 325 percent or at least 600 percent, the elastic recovery is not more than 80 percent. For certain of these embodiments, the elastic recovery is less than 60 percent.

For certain embodiments, including any one of the above article, kit, or method embodiments, the multi-layer polymeric film has an elastic recovery of less than 30 percent at a tensile load of 1.8 to 2.2 newtons after recovery from a maximum extension of at least 325 percent. For certain of these embodiments, the elastic recovery is after recovery from a maximum extension of at least 600 percent. For certain of these embodiments, where the maximum extension is at least 325 percent or at least 600 percent, the elastic recovery is less than 20 percent.

When the hardenable dental material can provide sufficient resistance to the recovery load less deformation of the hardenable dental article can be achieved. Paste hardness is one measure of the ability of a material to resist deformation, with greater hardness providing more resistance. For certain embodiments, including any one of the above article, kit, or method embodiments, the hardenable dental material has a paste hardness at 28° C. of at least 400 g and not more than 4000 g. For certain of these embodiments, the hardenable dental material has a paste hardness at 28° C. of at least 1000 g and not more than 4000 g. For certain of these embodiments where the paste hardness is at least 400 g, the paste hardness is at least 500 g and not more than 2500 g. For certain of these embodiments, the paste hardness is at least 500 g and not more than 1500. For certain of these embodiments, where the paste hardness is at least 1000 g, the paste hardness is at least 1200 g and not more than 2500 g.

For certain embodiments, including any one of the above article, kit, or method embodiments, the multi-layer polymeric film exerts a tensile load of not more than 30 newtons at a maximum extension of at least 325 percent. For certain of these embodiments, the tensile load at the maximum extension is not more than 20 newtons, preferably not more than 18 newtons.

Alternatively, for certain embodiments, including any one of the above article, kit, or method embodiments, the multi-layer polymeric film has a maximum extension of at least 600 percent. For certain of these embodiments, the multi-layer polymeric film exerts a tensile load of not more than 30 newtons at the maximum extension. For certain of these embodiments, the tensile load at the maximum extension is not more than 25 newtons.

Relatively soft hardenable dental materials, such as those having a paste hardness of at least 400 g but not more than 1000 g or 1200 g may be more easily processed. However, multi-layer films having a greater degree of stretch, as measured, for example, by tensile elongation, may be more useful for a wider range of hardenable dental articles, for example, articles with a wider range of height to base ratios, when using such relatively soft materials. For certain embodiments, films as described herein having a maximum extension of at least 600 percent may preferably be used with the relatively soft materials.

Protected hardenable dental articles described herein may include some small punctures (perforations or holes) in the multi-layer film when such defects do not render the article unusable, such as if the article were substantially deformed. However, for certain embodiments, including any one of the article, kit, and method embodiments described herein, preferably the radial stretching takes place without causing a puncture in the multi-layer polymeric film.

Multi-layer polymeric films used in the protected hardenable dental articles of the article, kit, and method embodiments described herein comprise at least two layers, which include a first outer layer and a second core layer. Each of these layers may be comprised of one, two, or more layers. For certain embodiments, the multi-layer polymeric film comprises at least three layers, including a first outer layer, a second core layer, and a third outer layer. Each of these layers may be comprised of one, two, or more layers. For certain of these embodiments, the first outer layer and the third outer layer exert substantially the same recovery load. With substantially the same recovery load on each major surface of the multi-layer film, any curl in the film or other defect caused by an imbalance in recovery loads after undergoing a strain, such as linear, biaxial or radial stretching, is reduced or eliminated. The outer layers, also known as skin layers, can be balanced even though the skin layers are different materials, different combinations of materials, and/or different thicknesses.

For certain of these embodiments, including any one of the article, kit, or method embodiments described herein, which include at least one outer layer, the outer layer or each of the outer layers independently have a thickness of not more than 20 micrometers. For certain of these embodiments, the thickness is not more than 15 micrometers. For certain of these embodiments, the thickness is not less than 2 micrometers. For certain of these embodiments, the thickness is not less than 3 micrometers. For certain of these embodiments, the thickness is not less than 4 micrometers.

For certain embodiments, including any one of the above article, kit, or method embodiments where the multi-layer polymeric film comprises a first outer layer and a second core layer, at least one of the first outer layer and the second core layer releases from the hardenable dental material without substantially deforming a shape of the hardenable dental article, and wherein at least one of the first outer layer and the second core layer release from a mold surface without substantially deforming the shape of the hardenable dental article. For certain of these embodiments, the second core layer contains a release additive distributed throughout the layer. Release additives include, for example, silicone oils. Other release additives include, for example, waxes and extrudable fluorochemical polymers. The first outer layer may optionally include a release additive, although it is preferred that a release additive which could migrate into the hardenable dental material not be included in a layer of the multi-layer film that is in contact with the hardenable dental material.

For certain embodiments, including any one of the above article, kit, or method embodiments where the multi-layer polymeric film includes a first outer layer, a second core layer, and a third outer layer, at least one of the first outer layer and the third outer layer releases from the hardenable dental material without substantially deforming a shape of the hardenable dental article, and wherein at least one of the first outer layer and the third outer layer release from a mold surface without substantially deforming the shape of the hardenable dental article. For certain of these embodiments, at least one of the first outer layer and the third outer layer contains a release additive distributed throughout the layer.

For certain embodiments, including any one of the above embodiments which includes at least one outer layer, suitable outer layers preferably comprise a thermoplastic polymer selected from the group consisting of high density polyethylene, low density polyethylene, very low density polyethylene, polypropylene, poly(ethylene-co-propylene), poly(ethylene-co-hexene), poly(ethylene-co-octene), poly(ethylene-co-butene), poly(ethylene-co-vinyl acetate), poly(ethylene-co-vinyl alcohol), a polyurethane, and a combination thereof. For certain of these embodiments, the thermoplastic polymer is selected from the group consisting of isotactic polypropylene, poly(ethylene-co-propylene) impact copolymer, high density polyethylene, and a combination thereof. A combination thereof includes copolymers and/or blends. For certain of these embodiments, the thermoplastic polymer is high density polyethylene.

For certain embodiments, including any one of the above article, kit, or method embodiments, which includes a second core layer in the multi-layer polymeric film, the second core layer comprises an elastic material, a plastic material, or a combination thereof, wherein the core layer has a tensile elongation at break value of at least 350 percent. For certain of these embodiments, preferably the core layer has a tensile elongation at break value of at least 650 percent. For certain of these embodiments, preferably the core layer has a tensile elongation at break value of at least 850 percent. For certain of these embodiments, the second core layer is comprised of a polymer selected from the group consisting of linear low density polyethylene, very low density polyethylene, ultra-low density polyethylene, styrene-isoprene-styrene block copolymers, styrene-ethylene-co-butylene-styrene block copolymers, elastomeric polyurethanes, poly(ethylene-co-vinyl acetate), ethylene-propylene elastomeric copolymers, ethylene-propylene-diene elastomeric terpolymers, poly(ethylene-co-hexane), poly(ethylene-co-octene), poly(ethylene-co-butane), and a combination thereof. For certain of these embodiments, the second core layer is comprised of a polymer selected from the group consisting of very low density polyethylene, ultra-low density polyethylene, styrene-isoprene-styrene block copolymers, styrene-ethylene-co-butylene-styrene block copolymers, and a combination thereof. A combination thereof includes copolymers and/or blends. For certain of these embodiments, the second core layer is comprised of ultra-low density polyethylene.

In some embodiments, the first or the second layer material may contain a nucleating agent to enhance the ductility and deformability of the resulting film. Nucleating agents are additives that provide sites for crystal formation in the polymer melt. Certain pigments can be used as nucleators. Certain other additives commonly found in colorants (such as calcium stearates) can be used as neutralized nucleators. The nucleating agent can be directly added during melt extrusion or added in the form of master batched pallets. A large number of compounds can be used to nucleate the thermoplastic materials disclosed in herein. The nucleating agents can be either (1) those that are dispersed in the polymer and remain as a solid particulate in the polymer melt, for example, organic dicarboxylic acid salts, or (2) those that dissolve in the polymer melt and phase separate during cooling to produce the heterogeneous nuclei, for example sorbitol and its derivatives.

When handling the protected hardenable dental article, whether removing the article from the mold, placing it in or removing it from a kit, applying the article, or removing the film from the hardenable or hardened dental article, having a portion of the multi-layer polymeric film extend away from the base of the article facilitates handling. For certain embodiments, including any one of the above article, kit, or method embodiments, the multi-layer polymeric film comprises a flange extending away from the hardenable dental article at its base.

An interior cavity in the protected hardenable dental article facilitates mating of the article with a prepared dental surface or structure, for example, a prepared tooth structure. In addition, assuring full contact of the article with all surfaces of the mold may be facilitated by forming the interior cavity under pressure. For certain embodiments, including any one of the above article, kit, or method embodiments, the article further comprises an interior cavity with inner surfaces extending from the base. For certain of these embodiments, where the multi-layer polymeric film comprises a flange extending away from the base, the hardenable dental article further comprises a base liner covering the interior cavity, the base, and at least a portion of the flange.

Certain films previously used in making protected hardenable dental articles have now been recognized as causing the base of the hardenable article to flare outward, causing the diameter of the base to increase and in some cases producing loose material (flash) at the margin of the base. This requires correction when the article is used. Accordingly, minimizing or eliminating flaring is a useful advantage. This can be accomplished using multi-layer films described herein with sufficiently high radial stretch or tensile elongation, sufficiently low load when fully stretched or elongated, and/or sufficiently low elastic recovery as described herein. For certain embodiments, including any one of the above article, kit, or method embodiments, preferably the base has an average percent flare of less than 12 percent. For certain of these embodiments, more preferably the base has an average percent flare of less than 6 percent. For certain of these embodiments, even more preferably, the base has an average percent flare of less than 1 percent.

A reduction in the quality of protected hardenable dental articles has also now been found to occur when the base of the article increases in dimension and the height of the article decreases after removal from the mold, and therefore, the dimensions of the article deviate from a target ratio of height to base dimensions. For example, certain preformed crowns can be described as having a target height and target average base diameter. The ratio of these, a target height to base ratio, can be 0.73 for a pediatric molar, 0.89 for an adult molar, 1.24 for an adult premolar, 1.51 for an adult canine, 1.6 for an adult maxillary incisor, and 2.1 for an adult mandibular incisor. Deviations from such ratios can be minimized or eliminated using multi-layer films described herein with sufficiently high radial stretch or tensile elongation, sufficiently low load when fully stretched or elongated, and/or sufficiently low elastic recovery as described herein. For certain embodiments, including any one of the above article, kit, or method embodiments, preferably the ratio of the height of the protected hardenable dental article to average diameter of the base of the protected hardenable dental article is within 80 percent of the ratio based upon the dimensions of the mold used to make the article. For certain of these embodiments, the ratio of the height to the average diameter of the base is within 90 percent of the ratio based upon the dimensions of the mold used to make the article.

For certain embodiments, the protected hardenable dental article described herein has a height to average base diameter ratio of at least 0.5. For certain of these embodiments, the ratio is at least 0.7. For certain of these embodiments, the ratio is at least 0.8. For certain of these embodiments, the ratio is at least 1.0. For certain of these embodiments, the ratio is at least 1.5.

For certain embodiments, the protected hardenable dental article described herein is selected from the group consisting of a preformed crown, a preformed inlay, a preformed onlay, a preformed bridge, a preformed veneer, a preformed orthodontic appliance, a preformed maxillofacial prosthesis, a preformed denture, a preformed artificial tooth, and a preformed tooth splint. For certain of these embodiments, the hardenable dental article is a preformed crown. The preformed crown can be solid crowns, such as those described in International Publication No. WO 2008/033758 (Jones et al.), symmetric crowns, such as those described in International Publication No. WO 2006/119003 (Karim et al.), multi-layer crowns, such as those described in International Publication No. WO 2008/033893 (Jones et al.), crowns with an interior cavity, such as those described in U.S. Patent Application Publication No. US 2005/0100868 (Karim et al.), or can be configured in any of the shapes described herein.

As indicated above, in one embodiment there is provided a kit comprising a plurality of protected hardenable dental articles including any one of those described herein. For certain of these embodiments, the plurality of protected hardenable dental articles includes a plurality of sizes of the protected hardenable dental articles. For example, where the kit includes a plurality of crowns, sizes may be determined by the diameter of the base and the height of each crown. For certain of these embodiments, the plurality of protected hardenable dental articles includes a plurality of shapes of the protected hardenable dental articles. For example, where the kit includes a plurality of crowns, shapes may be determined by the type of crown, such as an anterior incisor, a molar, and the like.

For certain embodiments, including any one of the embodiments of the kit, the plurality of protected hardenable dental articles includes a plurality of color shades of the protected hardenable dental articles. For example, the color shades may include a variety of color shades of teeth normally encountered by a practitioner. For certain of these embodiments, the protected hardenable dental articles are preformed crowns. For certain of these embodiments, the preformed crowns are selected from the group consisting of anterior preformed crowns, posterior preformed crowns, whole mouth crowns, and a combination thereof.

For certain embodiments, including any one of the embodiments of the kit, the kit further includes a tool selected from the group consisting of a measuring tool, a color shade guide, and a combination thereof. The tools may be used by the practitioner to select an appropriate hardenable dental article for a particular application. Such tools may be reusable, sterilizable, and/or disposable.

For certain embodiments, including any one of the kit embodiments described herein, the kit includes at least one protected dental article having a height to average diameter ratio of at least 1.0. For certain of these embodiments, the ratio is at least 1.5. For certain of these embodiments, the ratio is at least 2.0.

Figure 1B:
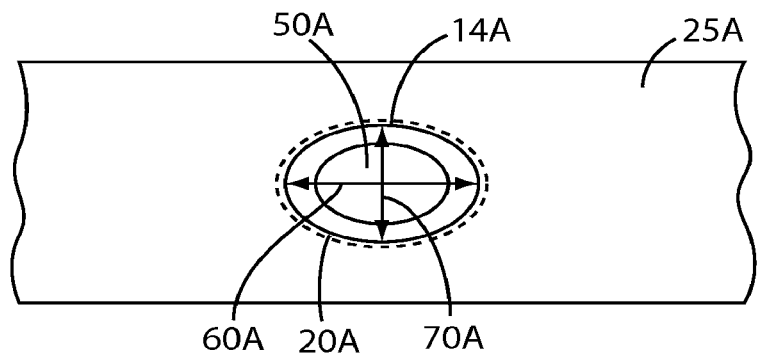
FIG. 1B is a top view of the protected hardenable dental article of FIG. 1.

In FIG. 1, one embodiment of a protected hardenable dental article 10 is illustrated in a cross-sectional view. Hardenable dental article 11, in the shape of a preformed anterior incisor crown, includes base 14 and outer surface 12 in intimate contact with multi-layer polymeric film 20. FIG. 1 also illustrates optional interior cavity 50 with inner surfaces 52 extending from base 14 in hardenable dental article 11 and optional base liner 40 covering base 14. Although base liner 40 is shown lining the interior cavity 50, alternatively, base liner 40, when present, can bridge interior cavity 50. With base liner 40 not present or after its removal, interior cavity 50 can be mated with a prepared tooth surface along with other materials as needed for proper spacing and bonding.

Flanges 25, also illustrated in FIG. 1, are an extension of multi-layer polymeric film 20, and although optional, in some embodiments flanges 25 are preferably present for ease of removing multi-layer polymeric film 20 from hardenable dental article 11 at an appropriate time. In certain embodiments, by pulling flanges 25 away from hardenable dental article 11 or its final hardened form, multi-layer polymeric film 20 can be conveniently removed. When base liner 40 is present, base liner 40 can cover the interior cavity, the base, and at least a portion of flanges 25. Flanges 25 and base liner 40 can optionally be used together to seal hardenable dental article 11 between multi-layer polymeric film 20 and base liner 40.

The base liner may be any film which releases from the hardenable dental material, since, at minimum, the base liner contacts the base of the hardenable dental article. For certain embodiments, including any one of the method embodiments described herein which includes a base liner, the base liner is any one of the embodiments described herein of the multi-layer polymeric film comprising at least two dissimilar polymers in separate layers. For certain embodiments, the base liner preferably also releases from a core pin used to create the interior cavity of the hardenable dental article. When the base liner lines the interior cavity of the hardenable dental article, the base liner is preferably a material which can undergo a high degree of elongation. For certain embodiments, including any one of the method embodiments described herein which includes a base liner, the base liner can be radially stretched to at least 350 percent of its unstretched area. For certain of these embodiments, preferably, the base liner can be radially stretched to at least 550 percent of its unstretched area. Homopolymer films and single layer films may be used. Suitable polymers include linear low density polyethylene, EVA copolymers, and the like. Moreover, for certain embodiments, preferably any of the embodiments of multi-layer polymeric films described herein can be used as the base liner.

FIG. 1A is a top view of the protected hardenable dental article of FIG. 1 with interior cavity 50A and without the base liner illustrated in FIG. 1. Flanges 25A extend from multi-layer polymeric film 20A at base 14A of the protected hardenable dental article. FIG. 1A also illustrates a diameter 60A of the hardenable dental article at its base 14A and a diameter 70A, which is perpendicular to diameter 60A. An average diameter of the base of the hardenable dental article can be determined by measuring the diameter 60A and the diameter 70A and averaging the measurements.

Figure 2A:
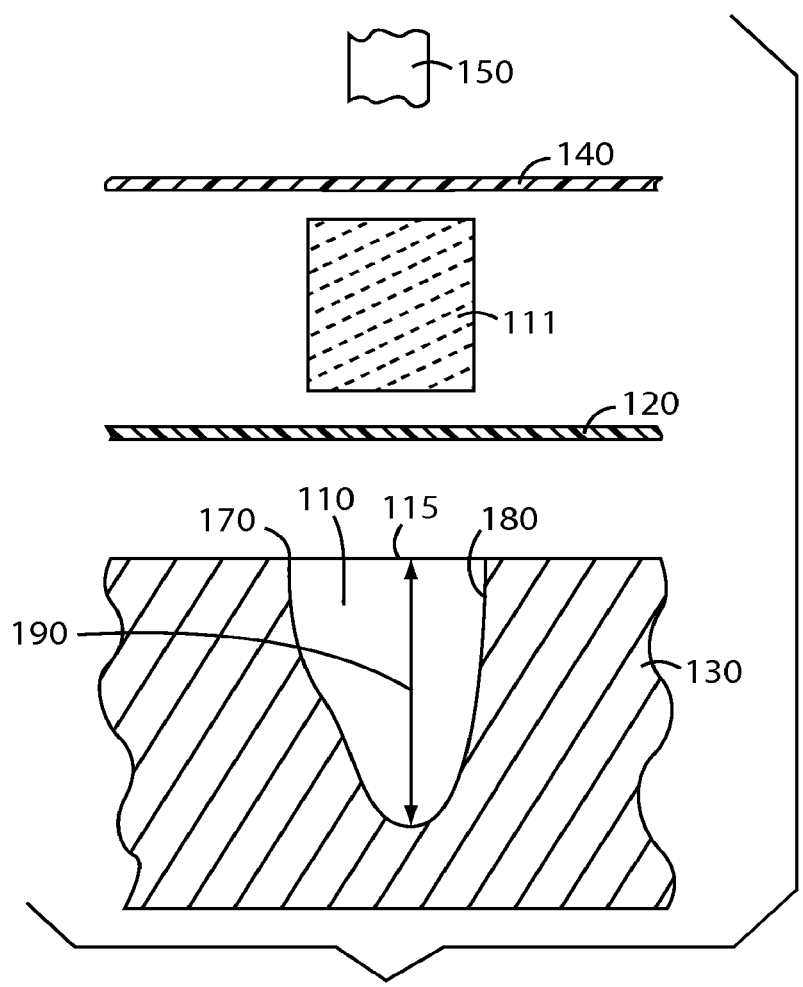
FIG. 2A is an exploded diagram in cross-section illustrating an embodiment of a method of manufacturing a protected hardenable dental article according to the present invention.
Figure 2B:
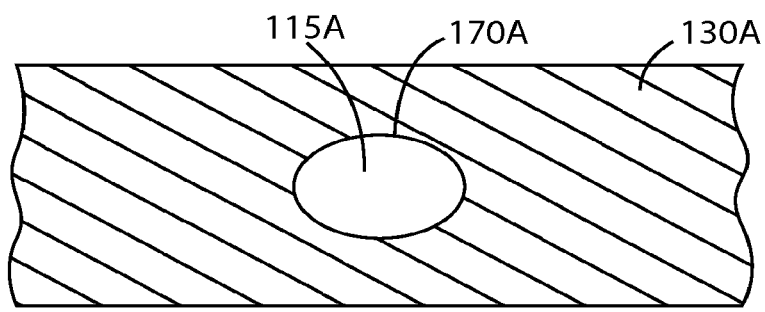
FIG. 2B is a top view of the opening into the mold cavity of FIG. 2.

FIG. 2 is a schematic cross-sectional diagram of one illustrative method of manufacturing the protected hardenable dental article of FIG. 1. The illustrated process includes a mold cavity 110 formed in a mold body 130. The mold cavity 110 in a shape of a hardenable dental article includes an opening 115 leading to the volume of the mold cavity 110 and surfaces 180 defining the shape, the surfaces 180 extending from the periphery 170 of opening 115. The mold cavity is depicted in cross-section in FIG. 2. In the depicted embodiment, the mold cavity 110 is in the shape of an anterior incisor dental crown. It should, however, be understood that the mold cavity 110 can have any dental shape to mimic, for example, an incisor, canine, pre-molar, molar, or other dental article.

FIG. 2A is a top view of mold body 130A, illustrating opening 115A with periphery 170A defining a target base diameter of the hardenable dental article. The target base diameter can be determined by measuring the average diameter of periphery 170A as described above in FIG. 1A. The target height of the hardenable dental article can be determined by measuring height 190 illustrated in FIG. 2. The target height can be divided by the average diameter of periphery 170A to provide a target height to base average diameter ratio. This can be compared with the height to average base diameter ratio of the hardenable dental article as described above. A difference between these ratios can be caused by a recovery force and elastic recovery exerted on the hardenable dental article by the radially stretched film.

The mold body 130 illustrated in FIG. 2 may be formed in any suitable material or combination of materials, e.g., metals, polymeric materials, etc. that provide sufficient structural integrity to withstand the forming process as described herein. In some instances, the mold body 130 may be formed in separable sections to facilitate positioning the multi-layer polymeric film and the hardenable dental material in mold cavity 110 and removal of a hardenable dental article formed therein. Also, the mold body 130 may be made of or coated with a material adapted to aid release of the hardenable dental article, with the multi-layer polymeric film covering substantially all of the outer surfaces of the hardenable dental article, from the interior surfaces of the mold cavity 110. For example, the interior surfaces of the mold cavity 110 may be coated with, e.g., fluorinated polymers (e.g., PTFE, etc.), boron carbide, chrome, thin dense chrome, chromium nitride, electroless nickel infused with fluorinated polymers, modified tungsten disulfide (e.g., DICRONITE), etc. For certain embodiments, preferably such coatings are not required because the multi-layer film releases from the mold surfaces without significant deformation of the hardenable dental article.

In other variations, the mold cavity 110 may be temperature controlled to assist in the molding process by, e.g., heating and/or cooling the interior surfaces of the mold cavity 110. In yet other variations, the mold cavity 110 may be vented or evacuated during the molding process to enhance molding. Ultrasonic or other vibrational energy may also be used to enhance filling of the mold cavity 110 and/or assist with releasing the article from the mold cavity 110.

In FIG. 2, multi-layer polymeric film 120 is disposed between the mold cavity and hardenable dental material 111, and film 120 and material 111 are forced (simultaneously or sequentially) into the mold cavity 110, wherein the multi-layer polymeric film 120 is between the hardenable dental material 111 and the surfaces 180 defining the shape, and wherein the hardenable dental material 111 is formed into the hardenable dental article having a base and outer surfaces extending from the base corresponding to the surfaces 180 defining the shape of the mold cavity. Hardenable dental material 111 can be provided in any shape or form that can be accommodated by mold cavity 110. Hardenable dental material 111 can optionally be provided as two or more layers of hardenable dental material, such that the resulting hardenable dental article has a different surface material, for example, a different color or different ultimate hardness capability, than interior material. Further examples of preformed, malleable, multi-layer hardenable dental articles are described in International Publication No. WO 2008/033893.

The process illustrated in FIG. 2 can be described as a compression molding process. It should, however, be understood that the hardenable dental material 111 may be formed into the hardenable dental article shape by other suitable processes. Some suitable processes may include, but are not limited to, e.g., injection molding, forging, casting, vacuum forming, extrusion molding, thermoforming, transfer molding, blow molding, etc.

An optional base liner 140 can be disposed over the hardenable dental material 111 such that the hardenable dental article is disposed between the multi-layer polymeric film and the base liner. Any one of the multi-layer polymeric film embodiments described herein can be used as the base liner. For certain embodiments, these two liners can provide a packaging for the preformed, malleable, hardenable dental article until it is used.

The method of manufacturing the protected hardenable dental article further includes removing the hardenable dental article from mold cavity 110, wherein multi-layer polymeric film 120 is in contact with at least a portion of the at least one outer surface; and wherein multi-layer polymeric film 120 comprises at least two dissimilar polymers in separate layers. For certain of these embodiments, multi-layer polymeric film 120 is in intimate contact with substantially all of the outer surfaces of the hardenable dental article; and multi-layer polymeric film 120 can be radially stretched by the hardenable dental article to an area which is at least 350 percent of the area of multi-layer polymeric film 120 prior to being radially stretched. Any one of the multi-layer polymeric film embodiments described herein may be used. For certain embodiments, as the height to average base diameter of the hardenable dental article is increased, multi-layer polymeric films with increased radial stretch or tensile elongation and reduced elastic recovery and recovery load are preferred.

The resulting protected hardenable dental article is ready to be used by a practitioner with the multi-layer polymeric film protecting the article. The practitioner may remove the film prior to or after application of the article to a prepared surface.

For certain embodiments, including any one of the above method embodiments, preferably the method further comprises locating multi-layer polymeric film 120 over opening 115 of mold cavity 110, wherein forcing hardenable dental material 111 and multi-layer polymeric film 120 into the mold cavity occur simultaneously.

Alternatively, for certain embodiments, the method further comprises locating multi-layer polymeric film 120 over opening 115 of mold cavity 110; and forcing multi-layer polymeric film 120 into mold cavity 110 before forcing hardenable dental material 111 into mold cavity 110. For certain of these embodiments, forcing multi-layer polymeric film 120 into mold cavity 110 comprises contacting substantially all of surfaces 180 extending from opening 115 with multi-layer polymeric film 120, and wherein multi-layer polymeric film 120 takes the shape of the hardenable dental article before forcing hardenable dental material 111 into mold cavity 110.

In another alternative, for certain embodiments, the method further comprises deforming multi-layer polymeric film 120 to form a pocket therein; and locating hardenable dental material 111 within the pocket before forcing hardenable dental material 111 and multi-layer polymeric film 120 into mold cavity 110. For certain of these embodiments, deforming multi-layer polymeric film 120 to form a pocket therein is carried out by forcing hardenable dental material 111 into contact with multi-layer polymeric film 120. For certain of these embodiments, the method further comprises providing an intermediate mold cavity 210 in body 230, illustrated in FIG. 3, mold cavity 210 dimensioned to fit within a mold cavity in the shape of the hardenable dental article such as the mold cavity illustrated in FIG. 2; forcing hardenable dental material 111 illustrated in FIG. 2 into contact with multi-layer polymeric film 220 and into intermediate mold cavity 210 to form pocket 250, now filled with hardenable dental material; and removing pocket 250 from intermediate mold cavity 210.

For certain embodiments, including the above methods which include forming a pocket containing hardenable dental material, forcing hardenable dental material 111 and multi-layer polymeric film 120 into the mold cavity comprises inserting the pocket into mold cavity 110 through opening 115 illustrated in FIG. 2.

Figure 3:
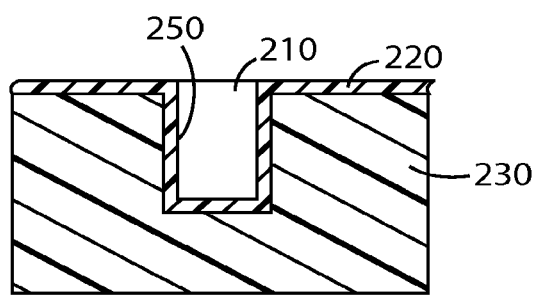
FIG. 3 is a cross-sectional view of an intermediate mold cavity with a multi-layer polymeric film formed to a pocket and hardenable dental material in the pocket.

Alternatively, for certain embodiments, forcing hardenable dental material 111 and multi-layer polymeric film 120 into mold cavity 110 comprises inserting the pocket, for example, pocket 250 illustrated in FIG. 3, into the mold cavity by closing mold cavity 110 around the pocket.

For certain embodiments, including any one of the above methods, forcing the hardenable dental material and the multi-layer polymeric film into the mold cavity comprises forcing a core pin, for example, core pin 150 illustrated in FIG. 2, against the hardenable dental material. For certain of these embodiments, the core pin forms an interior cavity, for example, interior cavity 50 illustrated in FIG. 1, within the hardenable dental article. For certain of these embodiments, the method further comprises providing a base liner, for example, optional base liner 140 illustrated in FIG. 2, between the hardenable dental material and the core pin. For certain of these embodiments, the base liner covers the base of the hardenable dental article.

For certain embodiments, including the above embodiments where the core pin forms an internal cavity within the hardenable dental article, the core pin permanently deforms the base liner when the core pin forms the interior cavity within the hardenable dental article, and the base liner lines the interior cavity, for example, as illustrated for base liner 40 in FIG. 1.

The core pin, such as core pin 150 in FIG. 2, can be configured to produce a variety of internal cavity shapes. For example, the core pin can be configured as a simple cylinder. In another example, the core pin can be configured to shape the internal cavity to at least partially parallel the external shape of the protected hardenable dental article. In other embodiments, the core pin is configured to shape the internal cavity to mate with a formed or prepared tooth surface. The multi-layer polymeric film can be used between the core pin and the hardenable dental material in forming such internal cavity shapes, thus providing the desired internal cavity shape and dimensions without significant deformation.

For certain embodiments, including any one of the above methods, the multi-layer polymeric film is any one of the embodiments of the multi-layer film described herein.

For certain embodiments, including any one of the above methods, the hardenable dental material is any one of the embodiments of the hardenable dental material described herein.

For certain embodiments, including any one of the above methods, the hardenable dental article is any one of the embodiments of the hardenable dental article described herein.

Exemplary Embodiments

1. A protected hardenable dental article comprising:
   a hardenable dental article comprising a base and at least one outer surface extending from the base, wherein at least the base and the at least one outer surface of the hardenable dental article comprise a hardenable dental material; and
   a multi-layer polymeric film in contact with at least a portion of the at least one outer surface; wherein the multi-layer polymeric film comprises at least two dissimilar polymers in separate layers.
2. The article embodiment 1, wherein the at least two dissimilar polymers differ from each other in a characteristic selected from the group consisting of composition, crystallinity, modulus, maximum elongation, recovery load, surface energy, an optical property, and a combination thereof.
3. The article of embodiment 1 or embodiment 2, wherein the separate layers have different thicknesses.
4. The article of any one of embodiments 1, 2, and 3, wherein the multi-layer polymeric film can be radially stretched by the hardenable dental article to an area which is at least 350 percent of the area of the multi-layer polymeric film prior to being radially stretched.
5. The article of embodiment 4, wherein the multi-layer polymeric film can be radially stretched by the hardenable dental article to an area which is at least 550 percent of the area of the multi-layer polymeric film prior to being radially stretched.
6. The article of embodiment 5, wherein the multi-layer polymeric film can be radially stretched by the hardenable dental article to an area which is at least 800 percent of the area of the multi-layer polymeric film prior to being radially stretched.
7. The article of any one of embodiments 1 through 5, wherein the multi-layer polymeric film is radially stretched by the hardenable dental article to an area 550 to 850 percent of the area of the multi-layer polymeric film prior to being radially stretched.

8. The article of any one of embodiments 1 through 7, wherein the multi-layer polymeric film has an elastic recovery of not more than 85 percent at a tensile load of less than 0.044 newtons after recovery from a maximum extension of at least 325 percent.
9. The article of embodiment 8, wherein the elastic recovery is after recovery from a maximum extension of at least 600 percent.
10. The article of embodiment 8 or embodiment 9, wherein the elastic recovery is less than 80 percent.
11. The article of any one of embodiments 1 through10, wherein the multi-layer polymeric film has an elastic recovery of less than 30 percent at a tensile load of 1.8 to 2.2 newtons after recovery from a maximum extension of at least 325 percent
12. The article of embodiment 11, wherein the elastic recovery is after recovery from a maximum extension of at least 600 percent.
13. The article of embodiment 11 or embodiment 12, wherein the elastic recovery is less than 20 percent.
14. The article of any one of embodiments 1 through 13, wherein the hardenable dental material has a paste hardness at 28° C. of at least 400 g and not more than 4000 g.
15. The article of any one of embodiments 1 through 14, wherein the multi-layer polymeric film exerts a tensile load of not more than 30 newtons at a maximum extension of at least 325 percent.
16. The article of any one of embodiments 1 through 15, wherein the multi-layer polymeric film has a maximum extension of at least 600 percent.
17. The article of embodiment 16, wherein the multi-layer polymeric film exerts a tensile load of not more than 30 newtons at the maximum extension.
18. The article of any one of embodiments 1 through 17, wherein the multi-layer polymeric film is radially stretched without causing a perforation in the multi-layer polymeric film.
19. The article of any one of embodiments 1 through 18, wherein the multi-layer polymeric film comprises at least two layers, including a first outer layer and a second core layer.
20. The article of embodiment 19, wherein at least one of the first outer layer and the second core layer releases from the hardenable dental material without substantially deforming a shape of the hardenable dental article, and wherein at least one of the first outer layer and the second core layer release from a mold surface without substantially deforming the shape of the hardenable dental article.
21. The article of embodiment 20, wherein the second core layer and optionally the first outer layer contain a release additive distributed throughout the layer.
22. The article of any one of embodiments 1 through 18, wherein the multi-layer polymeric film comprises at least three layers, including a first outer layer, a second core layer, and a third outer layer.
23. The article of embodiment 22, wherein the first outer layer and the third outer layer exert substantially the same recovery load.
24. The article of embodiment 22 or embodiment 23, wherein at least one of the first outer layer and the third outer layer releases from the hardenable dental material without substantially deforming a shape of the hardenable dental article, and wherein at least one of the first outer layer and the third outer layer release from a mold surface without substantially deforming the shape of the hardenable dental article.
25. The article of embodiment 24, wherein at least one of the first outer layer and the third outer layer contains a release additive distributed throughout the layer.
26. The article of any one of embodiments 19 through 25, wherein each outer layer comprises a thermoplastic polymer selected from the group consisting of high density polyethylene, low density polyethylene, very low density polyethylene, polypropylene, poly(ethylene-co-propylene), poly(ethylene-co-hexene), poly(ethylene-co-octene), poly(ethylene-co-butene), poly(ethylene-co-vinyl acetate), poly(ethylene-co-vinyl alcohol), a polyurethane, and a combination thereof.
27. The article of embodiment 26, wherein the thermoplastic polymer is selected from the group consisting of isotactic polypropylene, poly(ethylene-co-propylene) impact copolymer, high density polyethylene, and a combination thereof.
28. The article of any one of embodiments 19 through 27, wherein the second core layer comprises an elastic material, a plastic material, or a combination thereof, wherein the core layer has a tensile elongation at break value of at least 350 percent.
29. The article of embodiment 28, wherein the core layer has a tensile elongation at break value of at least 650 percent.
30. The article of embodiment 28 or embodiment 29, wherein the second core layer is comprised of a polymer selected from the group consisting of linear low density polyethylene, very low density polyethylene, ultra-low density polyethylene, styrene-isoprene-styrene block copolymers, styrene-ethylene-co-butylene-styrene block copolymers, elastomeric polyurethanes, poly(ethylene-co-vinyl acetate), ethylene-propylene elastomeric copolymers, ethylene-propylene-diene elastomeric terpolymers, poly(ethylene-co-hexane), poly(ethylene-co-octene), poly(ethylene-co-butane), and a combination thereof.
31. The article of embodiment 30, wherein the second core layer is comprised of a polymer selected from the group consisting of very low density polyethylene, ultra-low density polyethylene, styrene-isoprene-styrene block copolymers, styrene-ethylene-co-butylene-styrene block copolymers, and a combination thereof.
32. The article of any one of embodiments 1 through 31, wherein the multi-layer polymeric film comprises a flange extending away from the hardenable dental article at its base.
33. The article of any one of embodiments 1 through 32, further comprising an interior cavity with inner surfaces extending from the base.
34. The article of embodiment 33 as dependent on embodiment 32, further comprising a base liner covering the interior cavity, the base, and at least a portion of the flange.
35. The article of any one of embodiments 1 through 34, wherein the base has an average percent flare of less than 12 percent.
36. The article of embodiment 35, wherein the base has an average percent flare of less than 6 percent.
37. The article of embodiment 36, wherein the base has an average percent flare of less than 1 percent.
38. The article of any one of embodiments 1 through 37, wherein the hardenable dental material is a photopolymerizable composite comprising a resin system, a filler system, and an initiator system, and wherein the photopolymerizable composite is self-supporting and malleable.
39. The article of any one of embodiments 1 through 38, wherein the hardenable dental article is selected from the group consisting of a preformed crown, a preformed inlay, a preformed onlay, a preformed bridge, a preformed veneer, a preformed orthodontic appliance, a preformed maxillofacial prosthesis, a preformed denture, a preformed artificial tooth, and a preformed tooth splint.

40. The article of embodiment 39, wherein the hardenable dental article is a preformed crown.

41. A kit comprising a plurality of protected hardenable dental articles of any one of embodiments 1 through 40.

42. The kit of embodiment 41, wherein the plurality of protected hardenable dental articles includes a plurality of sizes of the protected hardenable dental articles.

43. The kit of embodiment 41 or embodiment 42, wherein the plurality of protected hardenable dental articles includes a plurality of shapes of the protected hardenable dental articles.

44. The kit of any one of embodiments 41, 42, and 43, wherein the plurality of protected hardenable dental articles includes a plurality of color shades of the protected hardenable dental articles.

45. The kit of any one of embodiments 41 through 44, wherein the protected hardenable dental articles are preformed crowns.

46. The kit of embodiment 45, wherein the preformed crowns are selected from the group consisting of anterior preformed crowns, posterior preformed crowns, whole mouth crowns, and a combination thereof.

47. The kit of embodiment 45 or embodiment 46, wherein the preformed crowns include anterior preformed crowns.

48. The kit of any one of embodiments 41 through 47, further including a tool selected from the group consisting of a measuring tool, a color shade guide, and a combination thereof.

49. A method of manufacturing a protected hardenable dental article, the method comprising:
providing a first mold cavity in a shape of a hardenable dental article, wherein the first mold cavity comprises an opening and surfaces defining the shape, the surfaces extending from the opening;
forcing a hardenable dental material and a multi-layer polymeric film into the first mold cavity, wherein the multi-layer polymeric film is between the hardenable dental material and the surfaces defining the shape, and wherein the hardenable dental material is formed into the hardenable dental article comprising a base and at least one outer surface extending from the base, the surface corresponding to the first mold cavity surfaces defining the shape; and
removing the hardenable dental article from the first mold cavity;
wherein the multi-layer polymeric film is in contact with at least a portion of the at least one outer surface; and wherein the multi-layer polymeric film comprises at least two dissimilar polymers in separate layers.

50. The method of embodiment 49, further comprising locating the multi-layer polymeric film over the opening of the first mold cavity, wherein forcing the hardenable dental material and the multi-layer polymeric film into the first mold cavity occur simultaneously.

51. The method of embodiment 49, further comprising locating the multi-layer polymeric film over the opening of the first mold cavity; and forcing the multi-layer polymeric film into the first mold cavity before forcing the hardenable dental material into the first mold cavity.

52. The method of embodiment 51, wherein forcing the multi-layer polymeric film into the first mold cavity comprises contacting substantially all of the surfaces extending from the opening with the multi-layer polymeric film, and wherein the multi-layer polymeric film takes the shape of the hardenable dental article before forcing the hardenable dental material into the first mold cavity.

53. The method of embodiment 49 or embodiment 50, further comprising:
deforming the multi-layer polymeric film to form a pocket therein; and
locating the hardenable dental material within the pocket before forcing the hardenable dental material and the multi-layer polymeric film into the first mold cavity.

54. The method of embodiment 53, wherein deforming the multi-layer polymeric film to form a pocket therein is carried out by forcing the hardenable dental material into contact with the multi-layer polymeric film.

55. The method of embodiment 54, further comprising:
providing an intermediate, second mold cavity dimensioned to fit within the first mold cavity in the shape of the hardenable dental article;
forcing the hardenable dental material into contact with the polymeric muli-layer film and into the intermediate, second mold cavity to form the pocket; and
removing the pocket from the intermediate, second mold cavity.

56. The method of any one of embodiments 53, 54, and 55, wherein forcing the hardenable dental material and the multi-layer polymeric film into the first mold cavity comprises inserting the pocket into the first mold cavity through the opening.

57. The method of any one of embodiments 53, 54, and 55, wherein forcing the hardenable dental material and the multi-layer polymeric film into the first mold cavity comprises inserting the pocket into the first mold cavity by closing the first mold cavity around the pocket.

58. The method of any one of embodiments 49 through 57, wherein forcing the hardenable dental material and the multi-layer polymeric film into the first mold cavity comprises forcing a core pin against the hardenable dental material.

59. The method of embodiment 58, wherein the core pin forms an interior cavity within the hardenable dental article.

60. The method of any one of embodiment 49 through 59, wherein a base liner covers the base of the hardenable dental article.

61. The method of embodiment 60, wherein the base liner is a multi-layer polymeric film comprising at least two dissimilar polymers in separate layers.

62. The method of embodiment 61, wherein the base liner can be radially stretched to an area which is at least 350 percent of the area of the base liner prior to being radially stretched.

63. The method of embodiment 61 or embodiment 62, wherein the base liner has at least one outer layer which contains a release additive distributed throughout the outer layer.

64. The method of any one of embodiments 60 through 63, as dependent on embodiment 59, further comprising providing the base liner between the hardenable dental material and the core pin.

65. The method of embodiment 64, wherein the core pin permanently deforms the base liner when the core pin forms the interior cavity within the hardenable dental article, and wherein the base liner lines the interior cavity.

66. The method of any one of embodiments 49 through 65, wherein the at least two dissimilar polymers differ from each other in a characteristic selected from the group consisting of composition, crystallinity, modulus, maximum elongation, recovery load, surface energy, an optical property, and a combination thereof.

67. The method of any one of embodiments 49 through 66, wherein the separate layers have different thicknesses.

68. The method of any one of embodiments 49 through 67, wherein the multi-layer polymeric film can be radially stretched by the hardenable dental article to an area which is at least 350 percent of the area of the multi-layer polymeric film prior to being radially stretched.

69. The method of embodiment 68, wherein the multi-layer polymeric film can be radially stretched by the hardenable dental article to an area which is at least 550 percent of the area of the multi-layer polymeric film prior to being radially stretched.

70. The method of embodiment 69, wherein the multi-layer polymeric film can be radially stretched by the hardenable dental article to an area which is at least 800 percent of the area of the multi-layer polymeric film prior to being radially stretched.

71. The method of any one of embodiments 49 through 69, wherein the multi-layer polymeric film is radially stretched by the hardenable dental article to an area 550 to 850 percent of the area of the multi-layer polymeric film prior to being radially stretched.

72. The method of any one of embodiments 49 through 71, wherein the multi-layer polymeric film has an elastic recovery of not more than 85 percent at a tensile load of less than 0.044 newtons after recovery from a maximum extension of at least 325 percent.

73. The method of embodiment 72, wherein the elastic recovery is after recovery from a maximum extension of at least 600 percent.

74. The method of embodiment 72 or embodiment 73, wherein the elastic recovery is less than 80 percent.

75. The method of any one of embodiments 49 through 74, wherein the multi-layer polymeric film has an elastic recovery of less than 30 percent at a tensile load of 1.8 to 2.2 newtons after recovery from a maximum extension of at least 325 percent.

76. The method of embodiment 75, wherein the elastic recovery is after recovery from a maximum extension of at least 600 percent.

77. The method of embodiment 75 or embodiment 76, wherein the elastic recovery is less than 20 percent.

78. The method of any one of embodiments 49 through 77, wherein the hardenable dental material has a paste hardness at 28° C. of at least 400 g and not more than 4000 g.

79. The method of any one of embodiments 49 through 78, wherein the multi-layer polymeric film exerts a tensile load of not more than 30 newtons at a maximum extension of at least 325 percent.

80. The method of any one of embodiments 49 through 79, wherein the multi-layer polymeric film has a maximum extension of at least 600 percent.

81. The method of embodiment 80, wherein the multi-layer polymeric film exerts a tensile load of not more than 30 newtons at the maximum extension.

82. The method of any one of embodiments 49 through 81, wherein the multi-layer polymeric film is radially stretched without causing a perforation in the multi-layer polymeric film.

83. The method of any one of embodiments 49 through 82, wherein the multi-layer polymeric film comprises at least two layers, including a first outer layer and a second core layer.

84. The method of embodiment 83, wherein at least one of the first outer layer and the second core layer releases from the hardenable dental material without substantially deforming a shape of the hardenable dental article, and wherein at least one of the first outer layer and the second core layer release from a mold surface without substantially deforming the shape of the hardenable dental article.

85. The method of embodiment 84, wherein the second core layer and optionally the first outer layer contain a release additive distributed throughout the layer.

86. The method of any one of embodiments 49 through 82, wherein the multi-layer polymeric film comprises at least three layers, including a first outer layer, a second core layer, and a third outer layer.

87. The method of embodiment 86, wherein the first outer layer and the third outer layer exert substantially the same recovery load.

88. The method of embodiment 86 or embodiment 87, wherein at least one of the first outer layer and the third outer layer releases from the hardenable dental material without substantially deforming a shape of the hardenable dental article, and wherein the other outer layer or both the first outer layer and the third outer layer release from the surfaces defining the shape of the mold cavity without substantially deforming the shape of the hardenable dental article.

89. The method of embodiment 88, wherein at least one of the first outer layer and the third outer layer contains a release additive distributed throughout the layer.

90. The method of any one of embodiments 83 through 89, wherein each outer layer comprises a thermoplastic polymer selected from the group consisting of high density polyethylene, low density polyethylene, very low density polyethylene, polypropylene, poly(ethylene-co-propylene), poly(ethylene-co-hexene), poly(ethylene-co-octene), poly(ethylene-co-butene), poly(ethylene-co-vinyl acetate), poly(ethylene-co-vinyl alcohol), polyurethanes, and a combination thereof.

91. The method of embodiment 90, wherein the thermoplastic polymer is selected from the group consisting of isotactic polypropylene, poly(ethylene-co-propylene) impact copolymer, high density polyethylene, and a combination thereof.

92. The method of any one of embodiments 83 through 91, wherein the second core layer comprises an elastic material, a plastic material, or a combination thereof, wherein the core layer has a tensile elongation at break value of at least 350 percent.

93. The method of embodiment 92, wherein the core layer has a tensile elongation at break value of at least 650 percent.

94. The method of embodiment 92 or embodiment 93, wherein the second core layer is comprised of a polymer selected from the group consisting of linear low density polyethylene, very low density polyethylene, ultra-low density polyethylene, styrene-isoprene-styrene block copolymers, styrene-ethylene -co-butylene-styrene block copolymers, elastomeric polyurethanes, ethylene-vinyl acetate copolymers, ethylene-propylene elastomeric copolymers, ethylene-propylene-diene elastomeric terpolymers, poly(ethylene-co-hexane), poly(ethylene-co-octene), poly(ethylene-co-butane), and a combination thereof.

95. The method of embodiment 94, wherein the second core layer is comprised of a polymer selected from the group consisting of very low density polyethylene, ultra-low density polyethylene, styrene-isoprene-styrene block copolymers, styrene-ethylene-co-butylene-styrene block copolymers, and a combination thereof.

96. The method of any one of embodiments 49 through 95, wherein the multi-layer polymeric film comprises a flange extending away from the hardenable dental article at its base.
97. The method of embodiment 96 as dependent on any one of embodiments 60 through 65 and 66 through 95 as dependent on any one of embodiments 60 through 65, wherein the base liner covers at least a portion of the flange.
98. The method of any one of embodiments 49 through 97, wherein the base has an average percent flare of less than 12 percent.
99. The method of embodiment 98, wherein the base has an average percent flare of less than 6 percent.
100. The method of embodiment 99, wherein the base has an average percent flare of less than 1 percent.
101. The method of any one of embodiments 49 through 100, wherein the hardenable dental material is a photopolymerizable composite comprising a resin system, a filler system, and an initiator system, and wherein the photopolymerizable composite is self-supporting and malleable.
102. The method of any one of embodiments 49 through 101, wherein the hardenable dental article is selected from the group consisting of a preformed crown, a preformed inlay, a preformed onlay, a preformed bridge, a preformed veneer, a preformed orthodontic appliance, a preformed maxillofacial prosthesis, a preformed denture, a preformed artificial tooth, and a preformed tooth splint.
103. The method of embodiment 102, wherein the hardenable dental article is a preformed crown.

Objects and advantages of this invention are further illustrated by the following examples, but the particular materials and amounts thereof recited in these examples, as well as other conditions and details, should not be construed to unduly limit this invention.

EXAMPLES

Test Methods

Paste Hardness

Hardness of the composite used in the Examples below was measured using a TEXTURE ANALYZER (available from Texture Technologies, Scarsdale, N.Y.). Approximately 1.2 g of paste was pressed into a cylindrical cup at a temperature of about 60° C. and allowed to equilibrate for a minimum of 20 minutes at 28° C. prior to testing. Testing was carried out at 28° C. and completed within one hour of pressing. The sample was tested by measuring the maximum force in grams needed to force a 2 mm diameter cylindrical probe into the sample at a rate of 1 mm/s to a depth of 1 mm. The test was repeated 4 times, and the average of the maximum force values was reported.

Film Testing

Films were tested on an INSTRON Tensile Tester Model 5500R (Norwood, Mass., USA), using variations on test method ASTM D882—Standard Test Method for Tensile Properties of Thin Plastic Sheeting. The test method was modified to measure film properties appropriate for different crown types. For posterior crowns, a test was run to a tensile engineering strain of 250% at 6.35 mm/s, followed by a hold at maximum extension of 10 s. The film was then allowed to recover at 4.23 mm/s to 0% strain, followed by stretch to 325% strain at 4.23 mm/s, a second 10 s hold at maximum extension, and a recovery to 0% strain at 4.23 mm/s. For anterior crowns, a similar test was run to extensions of 500% and 600%, respectively. Properties of interest in each test were the survival of the film to maximum extension, the tensile load at maximum extension, the extension (elastic recovery) at 2 N of recovery load (tensile load) after maximum extension, and the extension (elastic recovery) at ~0 N of recovery load (tensile load) after maximum extension (where 0 was defined as less than 0.044 N tensile load).

| Abbreviation | Description and Source of Material (Unless otherwise indicated, available from Sigma-Aldrich, St. Louis, MO.) |
| --- | --- |
| BisGMA | 2,2-bis[4-(2-hydroxy-3-methacryloyloxypropoxy)phenyl]propane (CAS No. 1565-94-2) |
| Polycaprylactone-IEM | two equivalents of 2-isocyanatoethyl methacrylate reacted with a hydroxy-terminated polycaprolactone diol, molecular weight of about 1250 g/mole (TONE 0230 formerly available from DOW Chemical Company. A substantially equivalent material can be prepared using CAPA 2205, available from Perstrop, Warrington, Cheshire, UK.) |
| TPEG-990 | ethoxylated glycerine having a number average molecular weight of 990 g/mole (DOW Chemical Company, Midland, MI) |
| Z250 Filler | zirconia silica filler of average particle size 0.6 to 0.9 micrometers treated with 3-methacryloxypropyltrimethoxysilane as described in U.S. Pat. No. 6,030,606 |
| CAB-O-SIL-M-5 | untreated amorphous fumed silica (Cabot Corp., Boston, MA) |
| IEM | 2-isocyanatoethyl methacrylate |
| CPQ | camphorquinone |
| TINUVIN P | 2-(2-hydroxy-5-methylphenyl)benzotriazole (available from Ciba-Geigy Corp, Hawthorne, NY) |
| BHT | 2,6-di-tert-butyl-4-methylphenol |
| EDMAB | ethyl 4-(N,N-dimethylamino)benzoate |
| DPIHFP (DPIPF$_6$) | diphenyl iodonium hexafluorophosphate (Johnson Matthey, Alfa Aesar Division, Ward Hill, NJ) |

Multi-Layer Polymeric Film Preparation

Elastomeric laminates were prepared by coextruding a sheet of elastomeric core material with two skin layers, one on either side of the core layer, as described in Example 1 of U.S. Pat. No. 6,869,666. The core and skin materials that were used, along with their suppliers, are summarized in the following Table 1 of materials.

TABLE 1

Table of Multi-layer polymeric film Materials

| Material Trade Designation | Supplier | Description | Placement in Construction |
|---|---|---|---|
| KRATON G1657 | KRATON[1] | S-EB-S[2] block copolymer | core |
| VECTOR 4111 | Dexco[3] | S-I-S[4] block copolymer | core |
| KRATON 1106 | KRATON | S-I-S block copolymer | core |
| PP 3445 | Exxon[5] | Isotactic polypropylene | skin |
| PP 7C12N | DOW Chemical[6] | PE-PP[7] impact copolymer | skin |
| PE 3150 | Equistar[8] | High-density polyethylene | skin |
| ENGAGE 8200G | DOW Chemical | Ultra low density polyethylene | core |
| M5865 | Equistar | High density polyethylene | skin |
| H6012 | Equistar | High density polyethylene | skin |
| M6030 | Equistar | High density polyethylene | skin |
| M6060 | Equistar | High density polyethylene | skin |
| LD728.61 | Exxon | Poly(ethylene-co-vinyl acetate) containing 19% vinyl acetate (EVA copolymer) | Comparative single layer film |

[1]KRATON Polymers, Houston, TX
[2]Styrene-ethylene/butylene-styrene
[3]Dexco Polymers, Houston, TX
[4]Styrene-isoprene-styrene
[5]EXXONMOBIL Chemical Company, Houston, TX
[6]DOW Chemical Company, Midland, MI
[7]Polyethylene-polypropylene
[8]Equistar Chemicals, Houston, TX Malleable Hardenable Dental Material Preparation A malleable curable composite (hardenable dental material) was prepared as described in Examples 1-14 of U.S. Patent Application Publication No. 2003/0114553 (Karim et al.) using the components described in Table 2. The composition of the composite is summarized in Table 2. The composite had a Paste Hardness of 567 g.

TABLE 2

Composite Composition

| Component | Percentage of Composition |
|---|---|
| BisGMA | 10.5498% |
| Polycaprolactone-IEM | 9.0960% |
| TPEG-990 | 0.6000% |
| Z-250 filler | 76.7302% |
| CAB-O-SIL M-5 | 2.1698% |
| CPQ | 0.0345% |
| EDMAB | 0.2032% |
| DIPHFP | 0.1016% |
| BHT | 0.0305% |
| TINUVIN P | 0.3048% |

Examples 1-25 and Comparative Example 1

Preparation of Preformed Hardenable Dental Articles

Preformed crowns were made by first forcing a known volume of composite against a sample film into an intermediate mold, bullet shaped and having a height of about 11.5 mm and a diameter of about 6.7 mm. The resulting pocket, formed in the shape of the intermediate mold and containing the composite within the sample film as illustrated in FIG. 3, was removed from the intermediate mold. The film was then evaluated for punctures, tears, or perforations by visual examination. If the film passed this first stage of radial stretching (stage 1), the composite in the pocket was subsequently formed into the shape of an anterior large maxillary incisor, with a target height of 13.1 mm. This was done by placing the pocket containing the composite into a mold cavity as illustrated in FIG. 2, placing a base liner over the composite, and forcing the base liner into the composite and the composite pocket into full contact with the mold cavity surfaces using a core pin as illustrated in FIG. 2. The ratio of the area of the resulting preformed crown (corresponding to the area of the mold cavity surfaces) to the unstretched area of the sample film which was stretched to the area of the preformed crown was 6.49:1. This corresponds to radially stretching the sample film to an area 649 percent of the area of the sample film prior to being radially stretched. Three to six preformed crowns as illustrated in FIG. 1 were prepared in each Example. Visual inspection of each preformed crown indicated that the height relative to the target height was acceptable for use. Each resultant preformed crown was subsequently stored for 24 hours, after which the preformed crown was examined for defects. A rating of pass indicated that the preformed crown was acceptable for use with no obvious defects. A rating of marginal indicated that there were obvious defects which did not render the preformed crown unusable. Such defects included minor deformation of the preformed crown, for example, a bend in a wall of the crown or a small amount of flash at the base and/or some small areas where the film had burst, for example, perforations up to 1 mm in diameter. A rating of fail indicated that there were obvious defects which rendered the preformed crown unusable. Such defects included gross deformation of the preformed crown, for example, the shape warped by more than 2 mm or a large amount of flash at the base, and/or large areas where the film had burst, for example, holes in the film which caused the composite paste to adhere to the mold, deforming the preformed crown on removal from the mold.

Evaluations of the preformed crowns made with the above composite are summarized in the following Table 3.

TABLE 3

Examples of Anterior Large Maxillary Incisor Preformed Crowns

| Example | Core Material Trade Designation | Core Thickness (μm) | Skin Material Trade Designation | Skin Thickness (μm) | Visual Score (a.u.) |
|---|---|---|---|---|---|
| CE-1 | LD 728.61 | 100 | n/a | n/a | Fail |
| 1 | VECTOR 4111 | 76.1 | PP 3445 | 8.05 | Pass |
| 2 | VECTOR 4111 | 77.1 | HDPE 3150 | 6.05 | Pass |
| 3 | VECTOR 4111 | 84 | HDPE 3150 | 3 | Pass |
| 4 | VECTOR 4111 | 62.2 | HDPE 3150 | 12 | Pass |
| 5 | KRATON 1106 | 88.9 | PP 3445 | 5.7 | Pass |
| 6 | KRATON 1106 | 91.8 | PP 3445 | 5.15 | Marginal |
| 7 | KRATON 1106 | 89.1 | PP 3445 | 3.45 | Marginal |
| 8 | KRATON 1106 | 134.8 | PP 7C12N | 7.05 | Pass |
| 9 | KRATON 1106 | 123.7 | PP 7C12N | 4.15 | Pass |
| 10 | KRATON 1106 | 130.8 | PP 7C12N | 2.4 | Marginal |
| 11 | KRATON 1106 | 130 | PP 7C12N | 7.6 | Pass |
| 12 | VECTOR 4111 | 199 | PP 7C12N | 4.15 | Marginal |
| 13 | KRATON G1657 | 41.1 | PP 3445 | 17.4 | Fail |
| 14 | KRATON G1657 | 39.7 | PP 3445 | 12.6 | Fail |
| 15 | ENGAGE 8200G | 65.3 | M6060 | 6.5 | Pass |
| 16 | ENGAGE 8200G | 68.5 | M6060 | 10 | Pass |
| 17 | ENGAGE 8200G | 57.1 | M6060 | 8.8 | Pass |
| 18 | ENGAGE 8200G | 57 | M6060 | 10 | Pass |
| 19 | ENGAGE 8200G | 70.2 | M6060 | 12 | Pass |
| 20 | ENGAGE 8200G | 44.3 | M6060 | 7.5 | Pass |
| 21 | ENGAGE 8200G | 57.7 | M6060 | 7.8 | Pass |
| 22 | ENGAGE 8200G | 63.7 | M5865 | 6.2 | Pass |
| 23 | ENGAGE 8200G | 69.5 | M5865 | 8 | Pass |

TABLE 3-continued

Examples of Anterior Large Maxillary Incisor Preformed Crowns

| Example | Core Material Trade Designation | Core Thickness (μm) | Skin Material Trade Designation | Skin Thickness (μm) | Visual Score (a.u.) |
|---|---|---|---|---|---|
| 24 | ENGAGE 8200G | 65.5 | M5865 | 10.5 | Pass |
| 25 | ENGAGE 8200G | 68.8 | M5865 | 14.6 | Pass |

CE-1 (Comparative Example 1) represents the result of using a monolayer film composed of the EVA copolymer. In CE-1, the film did not survive the stage 1 radial stretching, and no preformed crown was obtained. Examples 13 and 14 worked well in stage 1, but in these Examples there were obvious defects which rendered the preformed crowns unusable.

Examples 26-46, Comparative Examples 2-4

Multiple Crown Shape Evaluations

Films were prepared by coextrusion as described in Examples 1-25. The constructions of the films used in Examples 26-46 and Comparative Examples 2-4 are shown in the following Table 4.

TABLE 4

Film Constructions Used in Examples 26-46 and CE-2, 3, and 4

| Example Nos. | Core Material Trade Designation | Thickness | Skin Material Trade Designation | Thickness |
|---|---|---|---|---|
| 26, 33, 40 | VECTOR 4111 | 199 | PP 7C12N | 4.2 |
| 27, 34, 41 | KRATON 1106 | 88.9 | PP 3445 | 5.5 |
| 28, 35, 42 | VECTOR 4111 | 141.6 | PE 4023 | 18.1 |
| 29, 36, 43 | KRATON G1657 | 39.7 | PP 3445 | 12.6 |
| 30, 37, 44 | ENGAGE 8200G | 66.3 | HDPE M6060 | 6.4 |
| 31, 38, 45 | ENGAGE 8200G | 75.1 | HDPE M6060 | 12.5 |
| 32, 39, 46 | ENGAGE 8200G | 66 | PP7C12N | 6 |
| CE-2, CE-3, CE-4 | EVA copolymer single-layer film | 76.2 | n/a | n/a |

Each film was tested in two tensile tests; the first a two-stage cyclical elongation test to 250% and 325% total elongation (posterior film extension test), and the second a two-stage cyclical elongation test to 500 and 600% total elongation (anterior film extension test). These two tests are used in identify films suitable for forming posterior crowns and anterior crowns, respectively. Anterior crowns with a higher height to base diameter ratio require the film to possess more radial stretch capability than that required by posterior crowns.

Parameters obtained included the target maximum extension (actual maximum extension where the film did not achieve the target maximum extension), the tensile load at maximum extension, and the elastic recovery (%) at 2 newtons (N) and 0 N of tensile load. The maximum extension was of interest in order to determine if the film was capable of sufficient elongation to allow for the crown forming process. The load at maximum extension and the percent recovery at 2 N of tensile load were used to characterize the forces applied by the film to the crown after forming and removal from the mold. This force can result in deformation of the preformed crown over time, at least until the force is reduced to a point where the composite paste of the preformed crown is capable of supporting the applied load from the film. Results for these parameters for both tests are summarized in the following Tables 5 and 6.

TABLE 5

Posterior Film Extension Test Results (325% Extension)

| | 325% test | | | |
|---|---|---|---|---|
| Example Nos. | Max Extension (%) | Max Load (N) | % recovery (2N) | % recovery (~0N) |
| 26, 33, 40 | 325 | 10 | 71% | 93% |
| 27, 34, 41 | 325 | 9 | 6% | 80% |
| 28, 35, 42 | 325 | 8.6 | 51% | 86% |
| 29, 36, 43 | 325 | 15.6 | 6% | 44% |
| 30, 37, 44 | 325 | 13 | 18% | 53% |
| 31, 38, 45 | 325 | 16.9 | 14% | 51% |
| 32, 39, 46 | 325 | 16.4 | 17% | 48% |
| CE-2, CE-3, CE-4 | 325 | 29.8 | 13% | 47% |

TABLE 6

Anterior Film Extension Test Results (600% Extension)

| | 600% test | | | |
|---|---|---|---|---|
| Example Nos. | Max Extension (%) | Max Load (N) | % recovery (2N) | % recovery (~0N) |
| 26, 33, 40 | 600% | 16.1 | 81.2 | 94.7% |
| 27, 34, 41 | 600% | 15.3 | 9.3 | 77.0% |
| 28, 35, 42 | 600% | 15 | 63.8 | 91.0% |
| 29, 36, 43 | 534% | 26.1 | n/a | n/a |
| 30, 37, 44 | 600% | 20.1 | 12.5 | 35.0% |
| 31, 38, 45 | 600% | 22 | 13.3 | 53.3% |
| 32, 39, 46 | 566% | 27.9 | n/a | n/a |
| CE-2, CE-3, CE-4 | 378% | 37.8 | n/a | n/a |

Preformed crowns were formed in samples of each film by forcing a known volume of composite into an intermediate mold, wherein the composite is partially encased by the film as in Examples 1-25. The composite (paste) used was the composite as described in Table 2 above. The paste was subsequently formed into preformed crowns as described in Examples 1-25 except that the shapes of a maxillary molar, a maxillary incisor, and a mandibular incisor were used. The films used for forming these crowns underwent radial stretching of 571%, 649%, and 838%, respectively, based on the ratio of the initial to the final area of the film involved in the crown forming process. The film surrounding each preformed crown was visually examined for obvious punctures or tears. The crowns were also examined immediately after being formed for obvious visual defects which would impair their utility, and rated according to a 3-level scale; a failed crown exhibited visual defects that would render it undesirable or unusable for the dentist; a marginal crown exhibited minor defects which could easily be compensated for by the dentist; while a crown that passed was a useful crown free of visible minor defects.

The resulting preformed crowns were stored at ambient conditions for a minimum of 48 h to allow for film stress relaxation. The crowns were subsequently cured and measured using a digital micrometer, STARRETT model No. 2600-7 (L.S. STARRETT Corporation, Athol, Mass., USA). The micrometer used either opposing needle points or opposed flat platens for measuring, as appropriate for the given dimension. For anterior (incisor) crowns, the height of the crown was measured. For posterior (molar) crowns, a total of 5 dimensions were recorded; height of crown, dimension of base at parting line of the mold, dimension of base perpendicular to parting line of the mold, minimum diameter of crown wall along the parting line (PL) of the mold, and minimum diameter of the crown wall perpendicular to the PL of the mold. The base diameters and minimum diameters were averaged to obtain a representative value. A number of films, including those used in comparative examples CE-2, CE-3, and CE-4 caused an increased diameter at the base of the preformed crown relative to the minimum, a feature which is not in the design of a crown and not desired. This flaring at the base is believed to result from residual stresses in the film. The percent flare, which was determined on the maxillary molar crowns, was determined as the average % difference between the minimum wall diameter and the base diameter. The height to average base diameter ratio is defined as the ratio of the maximum height of the crown to the average of the base diameter in the mold parting line and perpendicular to mold parting line directions. Results are summarized in the following Tables 7, 8, and 9.

TABLE 7

Maxillary Incisor Crown Forming Evaluation, Examples 26-32 and CE-2

| | Maxillary Incisor | | |
|---|---|---|---|
| Example | Film Survival | Crown Quality | Height (mm) |
| 26 | Pass | Fail | 10.97 |
| 27 | Pass | Pass | 11.85 |
| 28 | Pass | Fail | n/a |
| 29 | Fail | Fail | n/a |
| 30 | Pass | Pass | 11.84 |
| 31 | Marginal | Marginal | 12.12 |
| 32 | Marginal | Marginal | 11.94 |
| CE-2 | Fail | Fail | n/a |

TABLE 8

Mandibular Incisor Crown Forming Evaluation, Examples 33-39 and CE-3

| | Mandibular Incisor | | |
|---|---|---|---|
| Example | Film Survival | Crown Quality | Height (mm) |
| 33 | Pass | Fail | 9.54 |
| 34 | Fail | Fail | n/a |
| 35 | Fail | Fail | n/a |
| 36 | Fail | Fail | n/a |
| 37 | Pass | Pass | 10.24 |
| 38 | Pass | Pass | 10.24 |
| 39 | Fail | Fail | n/a |
| CE-3 | Fail | Fail | n/a |

TABLE 9

Maxillary Molar Crown Evaluation, Examples 40-46 and CE-4

| Ex. | Film Survival | Crown Quality | Diameter at Mold PL (mm) 9.27 mm target Base | Min | Diameter Perpendicular to PL (mm) 9.83 mm target Base | Min | Height (mm) | Average % flare | Height to Ave. Base Diameter Ratio 0.89 target |
|---|---|---|---|---|---|---|---|---|---|
| 40 | Pass | Fail | 10.58 | 9.12 | 10.50 | 9.25 | 7.06 | 14.8% | 0.67 |
| 41 | Pass | Pass | 9.48 | 8.80 | 9.55 | 9.30 | 7.74 | 5.2% | 0.81 |
| 42 | Pass | Fail | 10.58 | 9.54 | 11.14 | 10.23 | 7.21 | 9.9% | 0.67 |
| 43 | Pass | Pass | 9.71 | 8.68 | 9.83 | 9.06 | 7.88 | 10.2% | 0.81 |
| 44 | Pass | Pass | 8.35 | 8.35 | 9.26 | 9.26 | 7.86 | 0% | 0.89 |
| 45 | Pass | Pass | 8.37 | 8.37 | 9.23 | 9.23 | 7.62 | 0% | 0.86 |
| 46 | Pass | Pass | 9.05 | 8.44 | 9.42 | 9.23 | 7.57 | 4.6% | 0.82 |
| CE-4 | Pass | Pass | 10.53 | 8.76 | 9.14 | 8.75 | 7.77 | 12.3% | 0.79 |

Examples 40 and 42 were not rated as "fail" due to perforations of the film, but rather due to residual stresses in the film causing deformation, as exhibited by the height to average base diameter ratio being significantly less than the target. As such, a stiffer paste would be expected to better resist these stresses, and prevent the excessive shrinkage in height and flaring at the base observed in this test. Percent flare values less than 12% are preferred.

Example 47

Preparation of Anterior Crown with Multi-Layer Film with Release Additive

A multilayer film was prepared as described in Example 1 of U.S. Pat. No. 6,869,666, using Kraton 1106 for the core and PP 3445 for the skin layers, except that the skin layers were a blend of isotactic polypropylene (PP 3445) with 4 percent by weight silicone oil (DC 200, viscosity of 5 centistokes at 25° C., DOW CORNING, Midland, MI) prepared by tumbling the isotactic polypropylene pellets with the silicone oil additive prior to feeding the pellets into the extruder. Anterior crowns were prepared using the soft composite as described in Examples 1-25, with a target height of 13.1 mm. Visual inspection of each preformed crown indicated that the height relative to the target height was acceptable for use. Each resultant preformed crown was subsequently stored for 24 hours, after which the preformed crown was examined for defects as in Examples 1-25. The results are shown in Table 10.

TABLE 10

Anterior Crown Made with Release Additive in Skin Layers of Film

| Example | Core | Core Thickness (μm) | Skin | Skin Thickness (μm) | Height (mm) | Visual Score (a.u.) |
|---|---|---|---|---|---|---|
| 47 | KRATON 1106 | 11.9 | PP 3445/ Silicone | 6.9 | 11.74 | Pass |

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the embodiments set forth herein.

The complete disclosures of the patents, patent documents, and publications cited herein are incorporated by reference in their entirety or the portions of each that are indicated as if each were individually incorporated.

What is claimed is:

1. A protected hardenable dental article comprising:
a hardenable dental article comprising a base and at least one outer surface extending from the base, wherein at least the base and the at least one outer surface of the hardenable dental article comprise a hardenable dental material; and
a multi-layer polymeric film conformable release liner in contact with at least a portion of the at least one outer surface; wherein the multi-layer polymeric film is removable from the hardenable dental article and comprises at least two dissimilar polymers in separate layers such that the multi-layer polymeric film comprises at least three layers, including a first outer layer, a second core layer, a third outer layer; and the multi-layer polymeric film exerts a tensile load of not more than 30 newtons at an extension from 325 to 600 percent and has an elastic recovery of not more than 85 percent at a tensile load of less than 0.044 newtons after recovery from an extension of 600 percent.

2. The article of claim 1, wherein the at least two dissimilar polymers differ from each other in a characteristic selected from the group consisting of composition, crystallinity, modulus, maximum elongation, recovery load, surface energy, an optical property, and a combination thereof.

3. The article of claim 1, wherein the multi-layer polymeric film is radially stretched to an area of at least 350 percent.

4. The article of claim 1, wherein the multi-layer polymeric film is radially stretched to an area of 550 to 850 percent.

5. The article of claim 1, wherein the multi-layer polymeric film has an elastic recovery of not more than 85 percent at a tensile load of less than 0.044 newtons after recovery from an extension of 325 percent.

6. The article of claim 1, wherein the multi-layer polymeric film has an elastic recovery of less than 30 percent at a tensile load of 1.8 to 2.2 newtons after recovery from an extension of 325 percent.

7. The article of claim 1, wherein each outer layer comprises a thermoplastic polymer selected from the group consisting of high density polyethylene, low density polyethylene, very low density polyethylene, polypropylene, poly(ethylene-co-propylene), poly(ethylene-co-hexene), poly(ethylene-co-octene), poly(ethylene-co-butene), poly(ethylene-co-vinyl acetate), poly(ethylene-co-vinyl alcohol), a polyurethane, and a combination thereof.

8. The article of claim 7, wherein the thermoplastic polymer is selected from the group consisting of isotactic polypropylene, poly(ethylene-co-propylene) impact copolymer, high density polyethylene, and a combination thereof.

9. The article of claim 1, wherein the second core layer comprises an elastic material, a plastic material, or a combination thereof, wherein the core layer has a tensile elongation at break value of at least 350 percent.

10. The article of claim 9, wherein the second core layer is comprised of a polymer selected from the group consisting of linear low density polyethylene, very low density polyethylene, ultra-low density polyethylene, styrene-isoprene-styrene block copolymers, styrene-ethylene-co-butylene-styrene block copolymers, elastomeric polyurethanes, poly(ethylene-co-vinyl acetate), ethylene-propylene elastomeric copolymers, ethylene-propylene-diene elastomeric terpolymers, poly(ethylene-co-hexane), poly(ethylene-co-octene), poly(ethylene-co-butane), and a combination thereof.

11. The article of claim 10, wherein the second core layer is comprised of a polymer selected from the group consisting of very low density polyethylene, ultra-low density polyethylene, styrene-isoprene-styrene block copolymers, styrene-ethylene-co-butylene-styrene block copolymers, and a combination thereof.

12. The article of claim 1, wherein the base has an average percent flare of less than 12 percent.

13. The article of claim 1, wherein the hardenable dental material is a photopolymerizable composite comprising a resin system, a filler system, and an initiator system, and wherein the photopolymerizable composite is self-supporting and malleable.

14. A kit comprising a plurality of protected hardenable dental articles of claim 1.

15. The article of claim 1, wherein the first outer layer and the third outer layer exert substantially the same recovery load.

16. The article of claim 1, wherein the first outer layer and the third outer layer comprise the same polymer.

17. The article of claim 1, wherein the first outer layer and the third outer layer have the same thickness.

18. The article of claim 1, wherein the multi-layer polymeric film is radially stretched without causing a perforation in the multi-layer polymeric film.

19. The article of claim 1, wherein the multi-layer polymeric film exerts a tensile load of not more than 30 newtons at an extension of 600 percent.

* * * * *